(12) United States Patent
Fujimoto et al.

(10) Patent No.: US 7,851,159 B2
(45) Date of Patent: Dec. 14, 2010

(54) METHOD FOR DETECTING TARGET NUCLEIC ACID WITH SPECIFIC BASE SEQUENCE AND SET OF NUCLEIC ACIDS FOR DETECTION

(75) Inventors: Kenzo Fujimoto, Nomi (JP); Yoshinaga Yoshimura, Ishikawa (JP); Shinzi Ogasawara, Ishikawa (JP)

(73) Assignee: Japan Science and Technology Agency, Saitama (JP)

(*) Notice: Subject to any disclaimer, the term of this patent is extended or adjusted under 35 U.S.C. 154(b) by 210 days.

(21) Appl. No.: 12/085,101

(22) PCT Filed: Nov. 17, 2006

(86) PCT No.: PCT/JP2006/323031

§ 371 (c)(1),
(2), (4) Date: May 16, 2008

(87) PCT Pub. No.: WO2007/058326

PCT Pub. Date: May 24, 2007

(65) Prior Publication Data

US 2009/0221429 A1    Sep. 3, 2009

(30) Foreign Application Priority Data

Nov. 17, 2005    (JP)    ............................. 2005-332424

(51) Int. Cl.
*C12Q 1/68* (2006.01)
*C07H 19/04* (2006.01)
*C07H 21/00* (2006.01)
*C07H 21/02* (2006.01)

(52) U.S. Cl. .................... 435/6; 536/23.1; 536/24.3; 536/24.33; 536/26.6

(58) Field of Classification Search .............. 435/6; 536/23.1, 24.3, 24.33, 26.6

See application file for complete search history.

(56) References Cited

U.S. PATENT DOCUMENTS 5,616,464 A    4/1997    Albagli et al.

(Continued)

FOREIGN PATENT DOCUMENTS

EP    1 125 945 A1    8/2001

(Continued)

OTHER PUBLICATIONS

K. Fujimoto et al., "Template-Directed Photoreversible Ligation of Deoxyoligonucleotides via 5-Vinyldeoxyuridine", *Journal of the American Chemical Society*, vol. 122, pp. 5646-5647 and Supporting Information S2-S24 (2000).

(Continued)

*Primary Examiner*—Jezia Riley
(74) *Attorney, Agent, or Firm*—Peter F. Corless; Weiying Yang; Edwards Angell Palmer & Dodge LLP

(57) ABSTRACT

It is intended to provide a method for detecting a target nucleic acid with a specific base sequence existing in a sample mixture with high specificity and sensitivity by utilizing the formation of a hybrid with a complementary strand as a detection principle, and a nucleic acid for the detection. The invention relates to a set of nucleic acids for detecting a target nucleic acid with a specific base sequence comprising a photoligating nucleic acid composed of a nucleic acid (with the proviso that in the nucleic acid, a nucleic acid and a peptide nucleic acid are included) having a group represented by the formula I, II, III, IV or V described in claims at the 5' end or 3' end as a base moiety, and a photoligated nucleic acid having a base with a carbon-carbon double bond at the 3' end or 5' end as a base moiety capable of photoligating to the photoligating nucleic acid, wherein either of the photoligating nucleic acid and the photoligated nucleic acid has a labeling moiety and the other remaining nucleic acid is immobilized on a substrate, and the method for detecting a target nucleic acid with a specific base sequence by using the set of nucleic acids.

40 Claims, 16 Drawing Sheets

Photoligation of $^{ZVC}$G-DNA

U.S. PATENT DOCUMENTS

| | | |
|---|---|---|
| 6,306,587 B1 | 10/2001 | Royer et al. |
| 6,573,048 B1 | 6/2003 | VanAtta et al. |
| 6,593,088 B1 | 7/2003 | Saito et al. |
| 2002/0018996 A1 | 2/2002 | Kimura et al. |

FOREIGN PATENT DOCUMENTS

| | | |
|---|---|---|
| JP | 2001-139594 | 5/2001 |
| JP | 2001-348398 | 12/2001 |
| WO | WO-2005/024386 A2 | 3/2005 |

OTHER PUBLICATIONS

M. Ogino et al., "Template-Directed DNA Photoligation via α-5-Cyanovinyldeoxyuridine", *Organic Letters*, 7(14), pp. 2853-2856 (2005).

Y. Yoshimura et al., "RNA template-directed photoligation via 5-carboxyvinyl-2'-deoxyuridine", *Nucleic Acids Symposium Series*, No. 49, pp. 143-144 (2004).

Ogasawara et al., Nucleic Acids Symposium Series, 49:145-146 (2005).

Saito et al., Tetrahedron Letters, 46:97-99 (2005).

S=Hexaethyleneglycol

Probe A ; 5'- ᶜᵛUCAGGTTCASSSS

Probe C ; 5'- ᶜᵛUCCGGTTCASSSS

Probe T; 5'- ᶜᵛUCTGGTTCASSSS

Probe G ; 5'- ᶜᵛUCGGGTTCASSSS

Table  MS data

| Entry | Calcd for [M+H]$^+$ | Found |
| --- | --- | --- |
| Probe A | 4356.26 | 4356.23 |
| Probe C | 4332.23 | 4332.26 |
| Probe G | 4372.26 | 4372.26 |
| Probe T | 4347.25 | 4347.25 |

Development of Reversible DNA Photoligation

Synthesis of 5-vinylcytosine-containing DNA $$\xrightarrow[\text{deprotection}]{\text{DNA synthsizer}} \quad 5'\text{-}^{Vinyl}CGCGTG$$

ESI TOF MASS
calc. 1833.36
found 1833.34

Reversible Photoligation of $^{3'}$T-DNA & $^{Vinyl}$C-DNA at 366 nm

Synthesis of $^{ZV}G$ monomer unit

Reagents and Conditions
a) DMF-dimethylacetal, DMF
b) Methylacrylate, Pd(OAc)$_2$, PPh$_3$, NEt$_3$, DMF
c) DMTrCl, DMAP, Pyridine
d) 2-Cyanoethyl tetraisopropylphosphoroamidite, Tetrazole, CH$_2$Cl$_2$

Post-Synthesis of $^{ZV}G$-containing ODNs

Photoligation of $^{ZVC}G$-DNA

Photosplitting of ligated ODN at 312 nm

Synthesis of $^{ZV}A$ monomer unit

Reagents and Conditions
a) Methylacrylate, Pd(PPh$_3$)$_4$, CuI, NEt$_3$, DMF, 70°C
b) DMF-dimethylacetal, DMF
c) DMTrCl, DMAP, Pyridine, r.t.
d) 2-Cyanoethyl tetraisopropylphosphoroamidite, Tetrazole, CH$_3$CN, 0°C-r.t.

Post-Synthesis of $^{ZV}A$-containing ODNs

Photoligation of $^{ZVA}$A-DNA

Photoligation of $^{ZVC}$A-DNA

Photosplitting of ligated ODN at 312 nm

UV Spectrum of $^{ZVC}A$

| λ (nm) | ε (l/mol.cm) |
|---|---|
| 270 | $5.42 \times 10^3$ |
| 322 | $5.50 \times 10^3$ |
| 366 | $8.2 \times 10^2$ |

SEQUENCE LISTING

<160> NUMBER OF SEQ ID NOS: 29

<210> SEQ ID NO 1
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1

```
cacgcaagca ca                                                          12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cacgcaagca ca                                                          12

<210> SEQ ID NO 3
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cacgcaugca ca                                                          12

<210> SEQ ID NO 4
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
cacgcaauca ca                                                          12

<210> SEQ ID NO 5
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cacgcaagua ca                                                          12

<210> SEQ ID NO 6
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cacgcaagcu ca                                                          12

<210> SEQ ID NO 7
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cacgcaagca ua                                                          12
```

```
<210> SEQ ID NO 8
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
cacgcaagaa ca                                                              12

<210> SEQ ID NO 9
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cacgcaagga ca                                                              12

<210> SEQ ID NO 10
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
cacgcgagca ca                                                              12

<210> SEQ ID NO 11
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
cacgccagca ca                                                              12

<210> SEQ ID NO 12
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
cacgcuagca ca                                                              12

<210> SEQ ID NO 13
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
```

-continued

```
<222> LOCATION: (7)..(7)
<223> OTHER INFORMATION: 5-carboxyvinyl-2'-deoxyuridine

<400> SEQUENCE: 13
tgtgctugcg tg                                                           12

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 5-carboxyvinyl-2'-deoxyuridine

<400> SEQUENCE: 14
acatgagtac gcugatggtg t                                                 21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, g, t, unknown or other

<400> SEQUENCE: 15
nnnnnnnnag cgtactcatg t                                                 21

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggcccatcct                                                              10

<210> SEQ ID NO 17
<211> LENGTH: 19
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 5-carboxyvinyl-2'-deoxyuridine

<400> SEQUENCE: 17
aggatgggcc ucaggttca                                                    19
```

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
aggatgggcc                                                          10

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
tgaacctgag gcccatcct                                                19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
tgaaccggag gcccatcct                                                19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
tgaacccgag gcccatcct                                                19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
tgaaccagag gcccatcct                                                19

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
tgaaccgagg cccatcct                                                 18

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cacgcargca ca                                                         12

<210> SEQ ID NO 25
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: vinyl-uridine

<400> SEQUENCE: 25
tgtgcyugcg tg                                                         12

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: vinyl-cytosine

<400> SEQUENCE: 26
tgtgctcgcg tg                                                         12

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 7-carboxyvinyl-7-deaza-2'-deoxyguanine

<400> SEQUENCE: 27
tgtgctggcg tg                                                         12

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: (E)-3-(4-amino-7-(4-hydroxy-5-

```
    (hydroxymethyl)tetrahydrofuran-2-yl)-7H-pyrrolo[2,3-d]pyrimidin-
    5-yl)acrylamide-adenosine

<400> SEQUENCE: 28
tgtgctagcg tg                                                    12

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (7)..(7)
<223> OTHER INFORMATION: 7-carboxyvinyl-7-deaza-2'-deoxyadenosine

<400> SEQUENCE: 29
tgtgctagcg tg                                                    12
```

METHOD FOR DETECTING TARGET NUCLEIC ACID WITH SPECIFIC BASE SEQUENCE AND SET OF NUCLEIC ACIDS FOR DETECTION

TECHNICAL FIELD

The present invention relates to a method for specifically detecting a target nucleic acid having a specific base sequence present in a sample mixture by adopting photoligation, and a set of nucleic acids for the detection.

BACKGROUND ART

As one of important fundamental means used in the field of genetic engineering, there may be mentioned detection (detection includes identification and quantification) of a nucleic acid (a nucleic acid includes a nucleic acid and a peptide nucleic acid) having a specific base sequence present in a sample mixture. By detecting the presence of a nucleic acid or a gene having a specific base sequence, it becomes possible to elucidate expression of a gene of interest and develop novel drugs, or to select cells or individuals transfected with a desired gene in gene recombination. It also becomes possible to diagnose or predict a disease before the onset or during the early phase of the disease by conducting genetic diagnosis and detecting any human genetic defect or alteration causing the disease.

In this way, detection of a nucleic acid having a specific base sequence present in a sample mixture is a fundamental means which is widely used in the field of genetic engineering, and for example, the following methods are known.

Initially, nucleic acid is extracted from cells that are desired for examination and a sample mixture solution of the nucleic acid is obtained. If needed, the nucleic acid is cleaved with appropriate restriction enzymes, and then subjected to electrophoresis, and membrane blotting is performed using the gel obtained therefrom. Subsequently, for a nucleic acid having a specific base sequence which is the aim of detection, a nucleic acid probe having a base sequence that is complementary to the specific base sequence is provided. Then, this nucleic acid probe is hybridized with the blotted nucleic acid. This nucleic acid probe is labeled in advance so as to become detectable. For example, the nucleic acid probe is labeled with a radioisotope. Thereby, a band of the nucleic acid hybridized with the nucleic acid probe is detected by autoradiography to confirm the presence of the target nucleic acid having a specific base sequence. This method, which is referred to as Northern Blotting in terms of RNA, and as Southern Blotting in terms of DNA, is still increasingly used while undergoing various modifications (description on the method is found in, for example, "Molecular Biology of the Cell" $4^{th}$ Ed., translated and supervised by Keiko Nakamura and Kenichi Matsubara, Newton Press, 2004, 494-500).

Furthermore, particularly in the recent technologies of genetic diagnosis, DNA chips (DNA microarrays) are used in the detection of nucleic acids having specific base sequences. A DNA chip has DNA probes having various base sequences immobilized and arranged in arrays in each of many compartments on a substrate. A mixture of DNA derived from a test subject is provided by labeling the DNA in advance, for example, by labeling the DNA with a fluorescent dye. This test subject-derived DNA mixture is added dropwise to the DNA chip to induce hybridization. In the test subject-derived DNA mixture, DNAs containing base sequences that are complementary to the DNA probes become fixed on the substrate of the DNA chip through the hybridization. These fixed test subject-derived DNAs are detected, for example, by means of the previous labeling with a fluorescent dye. In this method, various modifications are being achieved, such as conditioning of DNA, use of RNA, or normalization through competitive implementation of hybridization (description on the method is found in, for example, "Molecular Biology of the Cell" $4^{th}$ Ed., translated and supervised by Keiko Nakamura and Kenichi Matsubara, Newton Press, 2004, 533-535).

In this way, from the conventional methods as well as to the recent technologies, detection of a nucleic acid having a specific base sequence has long utilized hybridization with a nucleic acid probe having a complementary base sequence as the fundamental principle for enabling specific recognition of complementary base sequences. However, under the actual conditions for hybridization, it is difficult for the binding between a nucleic acid and a nucleic acid probe molecule to occur only with the nucleic acid having the target base sequence to hybridize a perfectly complementary strand. That is, it is known that formation of imperfect hybrid including certain mismatches occurs even with a nucleic acid having a non-target base sequence which is imperfect as a complementary strand, thus resulting in binding with a nucleic acid probe molecule. Such unintended binding with a nucleic acid probe emerges as noise in the detection stage. In order to increase the specificity of detection without the emergence of such noise, it is necessary to eliminate incomplete hybridization.

However, discrimination through hybridization makes use of the differences in thermal stability, and the difference between complete hybridization and incomplete hybridization lies only in the difference in thermal stability. For this reason, appropriate conditions for distinguishing the two states vary with the aimed base sequence, and even under appropriate conditions, the conditions for altering thermal stability have equal effects on both states. In other words, as long as the difference in the thermal stability of hybridization is used as the only principle for distinguishing the two states, certain noise has to be tolerated, while making a compromise in the balance between specificity and sensitivity of the detection.

Moreover, recently there is a demand for detection of a nucleic acid having a base sequence having a single base substitution for the purpose of development of novel drugs or genetic diagnosis. In particular, great expectation is posed on the technology of typing a single base polymorphism of DNA in the field of medical diagnostics. For this reason, it is especially demanded to achieve a balance between specificity to the extent of detecting a single base substitution, and a practicable sensitivity (S/N ratio).

Non-Patent Document 1: "Molecular Biology of the Cell" $4^{th}$ Ed., translated and supervised by Keiko Nakamura and Kenichi Matsubara, Newton Press, 2004, 494-500

Non-Patent Document 2: "Molecular Biology of the Cell" $4^{th}$ Ed., translated and supervised by Keiko Nakamura and Kenichi Matsubara, Newton Press, 2004, 533-535

DISCLOSURE OF THE INVENTION

It is an object of the present invention to provide a method for detecting a target nucleic acid having a specific base sequence present in a sample mixture by utilizing hybridization with a complementary strand while achieving a balance between high specificity and sensitivity (S/N ratio), and a nucleic acid for the detection.

For the above-mentioned object, the inventors of the present invention utilized photoligation for which research and development have been devotedly conducted by them for long years. The inventors found that the object can be achieved by combining hybridization and photoligation. That is, a molecule of nucleic acid having a labeling moiety can be covalently immobilized to a substrate using photoligation, by specifically photoligating the molecule only when complete hybridization is achieved. Further, as the molecule having a labeling moiety that is to be detected is immobilized to the substrate without depending on the maintenance of hybridization, thorough washing under a condition capable of dissociating complementary double strands has become possible. By this means, high specificity and sensitivity (S/N ratio) can be both achieved.

Therefore, the present invention relates to a set of nucleic acids for detecting a target nucleic acid having a specific base sequence, which the set of nucleic acids includes a photoligating nucleic acid comprising a nucleic acid (with the proviso that the nucleic acid includes a nucleic acid and a peptide nucleic acid) having a group represented by the following Formula I, Formula II, Formula III, Formula IV or Formula V:

[Formula I]

[Chemical Formula 1]

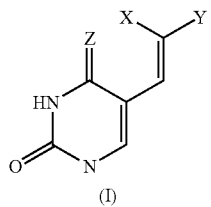

(I)

wherein Z represents O or NH; at least one of X and Y represents an electron-withdrawing group selected from the group consisting of a carboxyl group, a lower alkoxycarbonyl group, a substituted amide group and a cyano group; and the residue of X and Y represents a hydrogen atom,

[Formula II]

[Chemical Formula 2]

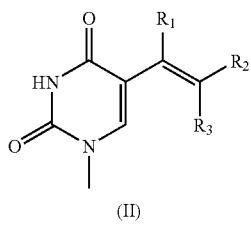

(II)

wherein $R_1$ is a hydrogen atom; at least one of $R_2$ and $R_3$ represents a group selected from the group consisting of a carboxyl group, a lower alkoxycarbonyl group, a lower alkenyl group, a lower alkynyl group, a substituted amide group, an amide group, a cyano group and a hydrogen atom; and the residue of $R_2$ and $R_3$ represents a hydrogen atom or a cyano group,

[Formula III]

[Chemical Formula 3]

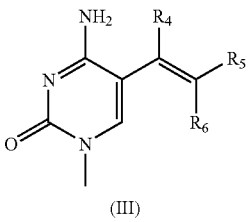

(III)

wherein $R_4$ is a hydrogen atom or a lower alkyl group; at least one of $R_5$ and $R_6$ represents a group selected from the group consisting of a carboxyl group, a lower alkoxycarbonyl group, a lower alkenyl group, a lower alkynyl group, a substituted amide group, an amide group, a cyano group and a hydrogen atom; and the residue of $R_5$ and $R_6$ represents a hydrogen atom or a cyano group,

[Formula IV]

[Chemical Formula 4]

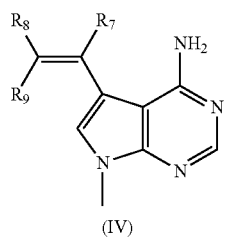

(IV)

wherein $R_7$ is a hydrogen atom or a lower alkyl group; at least one of $R_8$ and $R_9$ represents a group selected from the group consisting of a carboxyl group, a lower alkoxycarbonyl group, a lower alkenyl group, a lower alkynyl group, a substituted amide group, an amide group, a cyano group and a hydrogen atom; and the residue of $R_8$ and $R_9$ represents a hydrogen atom or a cyano group,

[Formula V]

[Chemical Formula 5]

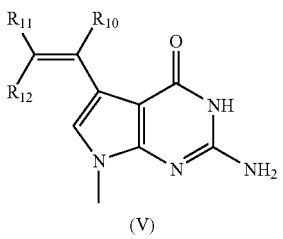

(V)

wherein $R_{10}$ is a hydrogen atom or a lower alkyl group; at least one of $R_{11}$ and $R_{12}$ represents a group selected from the group consisting of a carboxyl group, a lower alkoxycarbonyl group, a lower alkenyl group, a lower alkynyl group, a substituted amide group, an amide group, a cyano group and a hydrogen atom; and the residue of $R_{11}$ and $R_{12}$ represents a hydrogen atom or a cyano group, at the 5'-end or 3'-end as a base moiety, and a photoligated nucleic acid having a base having a carbon-carbon double bond at the 3'-end or 5'-end as a base moiety capable of being photoligated to the photoligating nucleic acid, wherein either one of the photoligating nucleic acid and the photoligated nucleic acid has a labeling moiety, while the other one not having a labeling moiety between the photoligating nucleic acid and the photoligated nucleic acid is immobilized on a substrate in advance;

a nucleic acid having a base sequence that is complementary to the base sequence of the target nucleic acid having a specific base sequence can be generated by allowing the photoligating nucleic acid to be photoligated to the photoligated nucleic acid; and the nucleic acid that can be generated by photoligation of the photoligating nucleic acid and the photoligated nucleic acid can be washed under a washing condition capable of dissociating complementary double strands.

In a preferred embodiment, the base moiety is a group represented by Formula I, and in the Formula I, Z is O, X is a hydrogen atom, and Y is a carboxyl group, a lower alkoxycarbonyl group, a substituted amide group or a cyano group.

In another preferred embodiment, the base moiety is a group represented by Formula II, and in the Formula II, at least one of $R_2$ and $R_3$ represents a group selected from the group consisting of a carboxyl group, a lower alkoxycarbonyl group, a substituted amide group, an amide group, a cyano group and a hydrogen atom, and the residue of $R_2$ and $R_3$ is a hydrogen.

In another preferred embodiment, the base moiety is a group represented by Formula III, and in the Formula III, at least one of $R_5$ and $R_6$ represents a group selected from the group consisting of a carboxyl group, a lower alkoxycarbonyl group, a substituted amide group, an amide group, a cyano group and a hydrogen atom, and the residue of $R_5$ and $R_6$ is a hydrogen atom.

In another preferred embodiment, the base moiety is a group represented by Formula IV, and in the Formula IV, at least one of $R_8$ and $R_9$ represents a group selected from the group consisting of a carboxyl group, a lower alkoxycarbonyl group, a substituted amide group, an amide group, a cyano group and a hydrogen atom, and the residue of $R_8$ and $R_9$ is a hydrogen atom.

In another preferred embodiment, the base moiety is a group represented by Formula V, and in the Formula V, at least one of $R_{11}$ and $R_{12}$ represents a group selected from the group consisting of a carboxyl group, a lower alkoxycarbonyl group, a substituted amide group, an amide group, a cyano group and a hydrogen atom, and the residue of $R_{11}$ and $R_{12}$ is a hydrogen atom.

As the label of the labeling moiety, it preferably comprises any label selected from the group consisting of biotin labels, dye labels (including fluorescent dye labels), RI labels, and enzyme labels (including chromogenic enzyme labels). It is particularly preferable to have a biotin label as the label of the labeling moiety.

It is preferable that either one of photoligating nucleic acid and the photoligated nucleic acid which is immobilized on a substrate in advance is immobilized on the substrate via a linker moiety.

The linker moiety preferably contains polyethylene glycol or an alkane. It is particularly preferable that the linker moiety contains polyethylene glycol.

The substrate is preferably any one selected from the group consisting of a glass plate, CPG, and polystyrene beads. It is particularly preferable that the substrate is a glass plate.

As for the washing condition, a condition which allows washing at a washing temperature in the range of 80° C. to 100° C. is preferred. As for the washing condition, a condition which allows washing at a washing temperature in the range of 95° C. to 100° C. is particularly preferred. As for the washing condition, a condition which allows washing with a washing solution containing a denaturing agent is preferred. An example of the denaturing agent may be urea.

As for the washing condition, a condition which allows washing with a washing solution containing a surfactant is preferred. An example of the surfactant may be sodium dodecyl sulfate.

The base having a carbon-carbon double bond is preferably cytosine, thymine or uracil.

The photoligating nucleic acid is suitably an oligonucleotide. The photoligating nucleic acid is suitably a DNA or an RNA. The photoligating nucleic acid is suitably a peptide nucleic acid.

The photoligated nucleic acid is suitably an oligonucleotide. The photoligated nucleic acid is suitably a DNA or an RNA. The photoligated nucleic acid is suitably a peptide nucleic acid.

It is suitable that the photoligating nucleic acid and the photoligated nucleic acid are nucleic acids of the same kind.

The target nucleic acid is suitably an oligonucleotide. The target nucleic acid is suitably a DNA or an RNA. The target nucleic acid is suitably a peptide nucleic acid.

The present invention also relates to a DNA microarray having either one of photoligating nucleic acid and the photoligated nucleic acid which does not have a labeling moiety is immobilized on a substrate in advance, and used together with the other one of photoligating nucleic acid and the photoligated nucleic acid which has labeling moiety (the molecule immobilized on a substrate includes a nucleic acid and a peptide nucleic acid, other than DNA).

The present invention also relates to a method for detecting (including identification and quantification) a target nucleic acid having a specific base sequence, present in a nucleic acid mixture, comprising the following steps of:

hybridizing a target nucleic acid having a specific base sequence contained in a nucleic acid mixture, with the photoligating nucleic acid and the photoligated nucleic acid;

immobilizing a nucleic acid having a labeling moiety on a substrate by photoirradiating the nucleic acid to result in photoligation of the nucleic acid with the photoligating nucleic acid and photoligated nucleic acid that have been brought adjacent in a manner capable of photoligating through the hybridization using the target nucleic acid having a specific base sequence as the template;

removing any nucleic acid having a labeling moiety and not immobilized on the substrate through photoligation by washing the nucleic acid having a labeling moiety and immobilized on the substrate through photoligation, under a washing condition capable of dissociating hybridized complementary double strands; and detecting the labeling moiety so as to detect the nucleic acid having a labeling moiety and immobilized on the substrate through photoligation.

It is preferable that the process of hybridization and the process of immobilizing a nucleic acid having a labeling moiety by photoligation are carried out at a temperature of 20° C. to 30° C.

It is preferable that the process of hybridization and the process of immobilizing a nucleic acid having a labeling moiety by photoligation are carried out in a reaction solution containing a salt having buffering effects. The pH value of the reaction solution is preferably in the range of 6.5 to 8.5. The concentration of the salt having buffering effects is preferably in the range of 5 to 250 mM. The salt having buffering effects is preferably cacodylic acid salt.

Furthermore, the reaction solution preferably contains a water-dispersible organic solvent. The reaction solution preferably contains 20% to 60% (by volume) of the water-dispersible organic solvent. The water-dispersible organic solvent is preferably acetonitrile.

It is also preferable that the reaction solution contains a salt of an alkali metal and/or alkaline earth metal, and the concentration of the salt is optimized with respect to the concentration of the target nucleic acid. Preferred examples of the salt of an alkali metal and/or alkaline earth metal include sodium chloride and/or magnesium chloride.

The washing condition preferably involves washing at a washing temperature in the range of 80° C. to 100° C., while it is particularly preferable that the washing condition involves washing at a washing temperature in the range of 95° C. to 100° C.

The washing condition preferably involves washing with a washing solution containing a denaturing agent, while it is particularly preferable that the washing condition involves washing with a washing solution containing a surfactant.

The photoirradiating is preferably performed by irradiation of light having a wavelength of 330 nm or longer.

The target nucleic acid is suitably an oligonucleotide. The target nucleic acid is suitably a DNA, and the target nucleic acid is also suitably an RNA. The target nucleic acid is suitably a peptide nucleic acid.

Furthermore, it is preferable that the label of the labeling moiety used in the above method is a fluorescent dye label, and the process of detecting the labeling moiety includes process of performing fluorescence measurement using a laser scanner.

It is also preferable that the label of the labeling moiety used in the method is a biotin label, and the process of the detecting the labeling moiety includes process of performing a biotin-avidin binding reaction using a fluorescent dye-labeled avidin and process of performing fluorescence measurement using a laser scanner.

The present invention also relates to a method for detecting point mutation in the base sequence of a target nucleic acid by using a photoligating nucleic acid and a photoligated nucleic acid, wherein a nucleic acid having a sequence having a single base substitution from a base sequence that is complementary to the base sequence of the target nucleic acid having a specific base sequence comprises a base sequence that would be generated by photoligation of the photoligating nucleic acid and the photoligated nucleic acid.

According to the present invention, a target nucleic acid having a specific base sequence present in a sample mixture can be detected by utilizing hybridization with a complementary strand as the principle of detection, while achieving a balance between high specificity and sensitivity. That is, since it is arranged such that photoligation can be achieved only when complete hybridization is implemented, only a molecule having a detectable labeling moiety can be covalently immobilized on a substrate. Therefore, thorough washing under a condition capable of dissociating complementary double strands has become possible. For this reason, noise can be largely reduced by completely eliminating unreacted substances. This does not cause any decrease in the detection sensitivity because the elimination is achieved without cleaving covalent bonds. That is, when incomplete hybridization is completely eliminated as such, high specificity and sensitivity can be both attained.

Therefore, the method for detecting a target nucleic acid having a specific base sequence, and the set of nucleic acids for the detection of the present invention provide both high specificity and sensitivity to all methods which utilize hybridization with a complementary base sequence as the principle.

Furthermore, in the present invention, the photoligation is a photoreaction, and does not necessitate establishment of subtle conditions such as the conditions for enzymatic reactions. The bonds generated therein are stable covalent bonds. For that reason, the present invention realizes the ease and efficiency of experimental operation, with which optimal conditions can be selected from an extremely broad range of conditions as the reaction conditions.

The high specificity and sensitivity of the present invention are useful in DNA typing, and are anticipated to be used in the field of medical diagnostics. In particular, the high specificity and sensitivity of the present invention is effective in detection of a single base substitution. Further, application of the present invention to a DNA chip has an advantage of high specificity and sensitivity, as well as advantages including high degree of freedom in the selection of the conditions for hybridization, high degree of freedom in the selection of temperature setting and convenient management compared to conventional detection methods involving hybridization or invader methods using enzymes. Thus, such application pioneers the use of DNA chips in a wider range of applications.

BEST MODE FOR CARRYING OUT THE INVENTION

Embodiments of the present invention will be described in detail in the following.

FIG. 1 is an explanatory diagram showing the flow of an embodiment of the present invention.

Part (1-1) of FIG. 1 shows ODN2($^{CV}$U) as a photoligating nucleic acid. This ODN2($^{CV}$U) is an oligonucleotide having 5-carboxyvinyl-2'-deoxyuridine (indicated as $^{CV}$U) as the base moiety of Formula I possessing photoligating properties. One end of this ODN2($^{CV}$U) is immobilized on the surface of a substrate via —N=CH—. Part (1-1) of FIG. 1 also shows biotin-ODN(T) as a photoligated nucleic acid. This biotin-ODN(T) is an oligonucleotide having thymine (indicated as T) as the base having a carbon-carbon double bond, which is the base moiety capable of being photoligated to the photoligating nucleic acid. This biotin-ODN(T) has biotin on one end as the labeling moiety. This biotin is represented by a circle on one end of the biotin-ODN(T) in FIG. 1. Part (1-1) of FIG. 1 also shows a target RNA(A) as the target nucleic acid having a specific base sequence.

This set of nucleic acids comprised of the target RNA(A) which is the target nucleic acid, ODN2($^{CV}$U) which is the photoligating nucleic acid and biotin-ODN(T) which is the photoligated nucleic acid is mixed to form hybrids. Then, with the target RNA(A) serving as a template, biotin-ODN(T) and ODN2($^{CV}$U) approach each other and align themselves so that T and $^{CV}$U can be photoligated according to the complementarity of the base sequences as arranged in advance. When photoirradiation is performed in this state, a photoreaction results in photoligation, and thus, as shown in Part (1-2) of FIG. 1, biotin-ODN(T) and ODN2($^{CV}$U) enter a state of being integrated into one by covalent bonding (the photoligated state is indicated with symbol "<", so that T and $^{CV}$U are crosslinked).

According to the finding of the inventors of the present invention as will be described later, in order to achieve photoligation as such, it is required that base sequences form a hybrid in a nearly perfectly complementary manner. This photoligation is impeded even by the incomplete hybridization resulting from merely a single base substitution. Thus, in the present invention, the high distinguishability for complementary strand due to this photoligation contributes to the high specificity obtained in the present invention.

When a state in which the labeling moiety is immobilized on a substrate through photoligation as such (Part (1-2) of FIG. 1) is achieved, the target nucleic acid (target RNA(A) of FIG. 1) which is already considered as a template, no longer needs to maintain the hybridized state. There, washing is subsequently performed under a condition capable of dissociating complementary double strands obtained by hybridization. Especially, in the present invention, even if the unintended, imperfect complementary double strands resulting from incomplete hybridization as well as the desired perfectly complementary double strands resulting from complete hybridization are dissociated and removed by washing, detection thereafter is not at all affected in principle. In other words, washing under a condition capable of dissociating perfectly complementary double strands is possible. For this reason, even if there were a labeling moiety weakly immobilized on a substrate via a base sequence analogous to the specific base sequence of the target RNA(A) by an incomplete hybridization to the extent that photoligation does not occur, it would be possible to completely remove this weakly immobilized labeling moiety and prevent it from appearing as noise. That is, in the present invention, reduction of noise achieved by washing under a washing condition capable of dissociating even desired complementary double strands obtained by hybridization contributes to the high sensitivity (S/N ratio) of the present invention.

Subsequently, detection is performed for the labeling moiety immobilized on the substrate through photoligation as such. Part (1-3) of FIG. 1 shows a figure of detecting biotin-ODN(T) by binding streptavidin-Cy3 thereto. Streptavidin strongly binds to biotin which is the labeling moiety, thereby detection is performed by reading the fluorescence of fluorescent dye Cy3 immobilized on the substrate, for example, with a laser scanner.

FIG. 8 is an explanatory diagram showing another embodiment of the present invention. FIG. 8 shows only the figure corresponding to Part (1-2) of FIG. 1 for the convenience of illustration. In FIG. 8, ODN P1 is shown as the photoligating nucleic acid. This ODN P1 is an oligonucleotide having 5-carboxyvinyl-2'-deoxyuridine (indicated as $^{CV}U$) as the base moiety of Formula I possessing photoligating properties. One end of this ODN2($^{CV}U$) is immobilized on the surface of a substrate via hexa(ethylene glycol) (S). FIG. 8 also shows ODN S35 as a photoligated nucleic acid. This ODN S35 is an oligonucleotide having cytosine (indicated as C) as the base having a carbon-carbon double bond, which is the base moiety capable of being photoligated to the photoligating nucleic acid. This ODN S35 has biotin (B) on one end as the labeling moiety.

In FIG. 8, these ODN P1 and ODN S35 are already being arranged adjacently to each other in a state where photoligation can be achieved through hybridization using a target oligonucleotide (Template ODN) as the template. Photoligation takes place when photoirradiation is performed in this state.

In the present invention, detailed examination has been conducted on the conditions for these hybridization and photoirradiation. Extensive examination on these conditions, namely, for example, temperature, the type and concentration of solvent (solute), salt or the like, is made possible because immobilization of a labeling moiety is carried out by a photoreaction such as photoligation in the present invention. In a method using an enzyme, such as a so-called invader method, there are restrictions in the optimal reaction conditions for the enzyme, therefore, it is impossible in principle to conduct an examination of reaction conditions focused on hybridization only. Thus, making it possible to select the reaction conditions for hybridization and photoligation with a high degree of freedom, and thereby making it possible to detect with higher specificity and sensitivity (S/N ratio), are benefits of the present invention.

Particularly in the present invention, it has been elucidated that the processes of hybridization and photoligation can be carried out very rapidly by using a water-dispersible organic solvent, for example, acetonitrile. It has been also elucidated that by using cacodylic acid buffer solution as the buffer solution, a fluorescence intensity exceeding 10-folds the conventional fluorescence intensity is obtained stably. It is also clarified that there is a correlation of optimal conditions between the target nucleic acid and the salt concentration, and the two factors respectively have different maximum values. That is, realizing very high specificity and sensitivity (S/N ratio) which is even higher than what is conventionally conceived by combining the reaction conditions selected with such high degree of freedom, is also a contribution brought by the present invention.

As such, after performing photoligation through hybridization, thorough washing is performed to remove the identification moiety (unreacted nucleic acid) attached by incomplete hybridization. Thereafter, detection is performed using a scanner by, for example, binding fluorescent avidin to the biotin moiety. Through such performance, perfect complementary sequences and the respective substituted sequences for sequences having a single base substitution, a two-base substitution or a three-base substitution can be distinguished with very high specificity and sensitivity (S/N ratio).

Embodiments of the present invention will be described in more detail as the following.

In a preferred embodiment, the photoligating nucleic acid has a group represented by the following Formula I:

[Formula I]

[Chemical Formula 6]

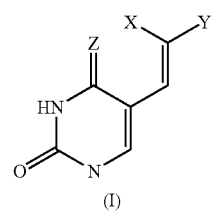

(I)

wherein Z represents O or NH; at least one of X and Y represents an electron-withdrawing group selected from the group consisting of a carboxyl group, a lower alkoxycarbonyl group, a substituted amide group and a cyano group; and the residue of X and Y represents a hydrogen atom; as a base moiety. The alkyl group in the alkoxycarbonyl group may be exemplified by a lower alkyl group having 1 to 10 carbon atoms, preferably 1 to 5 carbon atoms. Both of the substituents X and Y may be identical or different electron-withdrawing groups at the same time. Alternatively, only one of the substituents X and Y may be an electron-withdrawing group, while the other may be a hydrogen atom. In Formula I, it is preferable that Z is O; X is a hydrogen atom; and Y is a carboxyl group, a lower alkoxycarbonyl group, a substituted amide group or a cyano group. As a particularly preferred base moiety, 5-vinyl-2'-deoxyuridine and 5-carboxyvinyl-2'-deoxyuridine may be mentioned. 5-Carboxyvinyl-2'-deoxyuridine is particularly preferred.

In another preferred embodiment, the photoligating nucleic acid has a group represented by the following Formula II:

[Formula II]

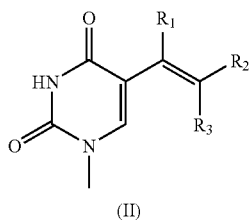

[Chemical Formula 7]

wherein $R_1$ is a hydrogen atom; at least one of $R_2$ and $R_3$ represents a group selected from the group consisting of a carboxyl group, a lower alkoxycarbonyl group, a lower alkenyl group, a lower alkynyl group, a substituted amide group, an amide group, a cyano group and a hydrogen atom; and the residue of $R_2$ and $R_3$ represents a hydrogen atom or a cyano group; as a base moiety.

At least one of $R_2$ and $R_3$ is preferably a carboxyl group, while a combination of a carboxyl group and a hydrogen atom is preferred as the combination of $R_2$ and $R_3$.

At least one of $R_2$ and $R_3$ is preferably a lower alkoxycarbonyl group, and the alkyl moiety in the lower alkoxycarbonyl group may be exemplified by lower alkyl having 1 to 10 carbon atoms, preferably 1 to 5 carbon atoms, more preferably 1 to 3 carbon atoms, even more preferably 1 to 2 carbon atoms, and particularly preferably one carbon atom. That is, preferred examples of the lower alkoxycarbonyl group include a methoxycarbonyl group, an ethoxycarbonyl group, a propoxycarbonyl group, a butoxycarbonyl group and the like. A methoxycarbonyl group, an ethoxycarbonyl group and a propoxycarbonyl group are more preferred; a methoxycarbonyl group and an ethoxycarbonyl group are even more preferred; and a methoxycarbonyl group is particularly preferred. A combination of a lower alkoxycarbonyl group and a hydrogen atom, particularly a combination of a methoxycarbonyl group and a hydrogen atom are preferred as the combination of $R_2$ and $R_3$.

At least one of $R_2$ and $R_3$ is preferably a lower alkenyl group, and the lower alkenyl group may be exemplified by a lower alkenyl group having 2 to 10 carbon atoms, preferably 2 to 5 carbon atoms, more preferably 2 to 3 carbon atoms, and particularly preferably 2 carbon atoms. A combination of a lower alkenyl group and a hydrogen atom, particularly a combination of a vinyl group and a hydrogen atom are preferred as the combination of $R_2$ and $R_3$.

At least one of $R_2$ and $R_3$ is preferably a lower alkynyl group, and the lower alkynyl group may be exemplified by a lower alkynyl group having 2 to 10 carbon atoms, preferably 2 to 5 carbon atoms, more preferably 2 to 3 carbon atoms, and particularly preferably 2 carbon atoms. A combination of a lower alkynyl group and a hydrogen atom, particularly a combination of an ethynyl group and a hydrogen atom are preferred as the combination of $R_2$ and $R_3$.

At least one of $R_2$ and $R_3$ is preferably substituted amide, and the substituted amide may be exemplified by mono-substituted, N-substituted amide. Preferred examples thereof include N-alkylamide and N-aminoalkylamide. Such N-alkylamide or N-aminoalkylamide is preferably a compound having 1 to 10 carbon atoms, preferably 1 to 5 carbon atoms, more preferably 1 to 3 carbon atoms, and particularly preferably 3 carbon atoms, and N-aminoalkylamide is particularly preferred. A combination of substituted amide and a hydrogen atom, particularly a combination of N-amino($C_1$-$C_3$ alkyl)amide and a hydrogen atom are preferred as the combination of $R_2$ and $R_3$.

At least one of $R_2$ and $R_3$ is preferably an amide group, and a combination of an amide group and a hydrogen atom is preferred as the combination of $R_2$ and $R_3$.

At least one of $R_2$ and $R_3$ is preferably a cyano group, and a combination of a cyano group and a cyano group, and a combination of a cyano group and a hydrogen atom are preferred as the combination of $R_2$ and $R_3$.

At least one of $R_2$ and $R_3$ is preferably a hydrogen atom, and a combination including at least one hydrogen atom, and a combination of a hydrogen atom and a hydrogen atom are preferred as the combination of $R_2$ and $R_3$.

In another preferred embodiment, the photoligating nucleic acid has a group represented by the following Formula III:

[Formula III]

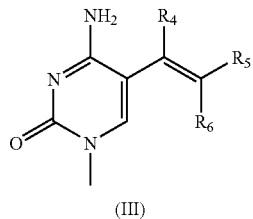

[Chemical Formula 8]

wherein $R_4$ is a hydrogen atom or a lower alkyl group; at least one of $R_5$ and $R_6$ represents a group selected from the group consisting of a carboxyl group, a lower alkoxycarbonyl group, a lower alkenyl group, a lower alkynyl group, a substituted amide group, an amide group, a cyano group and a hydrogen atom; and the residue of $R_5$ and $R_6$ represents a hydrogen atom or a cyano group; as a base moiety.

$R_4$ is particularly preferably a hydrogen atom.

$R_4$ is preferably a lower alkyl group, and the lower alkyl group is a group having 1 to 5 carbon atoms, preferably 1 to 3 carbon atoms, more preferably 1 to 2 carbon atoms, and particularly preferably one carbon atom. Such lower alkyl group may be exemplified by a methyl group, an ethyl group, a propyl group or the like, and a methyl group and an ethyl group are preferred, while a methyl group is particularly preferred.

At least one of $R_5$ and $R_6$ is preferably a carboxyl group, and a combination of a carboxyl group and a hydrogen atom is preferred as the combination of $R_5$ and $R_6$.

At least one of $R_5$ and $R_6$ is preferably a lower alkoxycarbonyl group, and the alkyl moiety in the lower alkoxycarbonyl group may be exemplified by lower alkyl having 1 to 10 carbon atoms, preferably 1 to 5 carbon atoms, more preferably 1 to 3 carbon atoms, even more preferably 1 to 2 carbon atoms, and particularly preferably one carbon atom. That is, preferred examples of the lower alkoxycarbonyl group include a methoxycarbonyl group, an ethoxycarbonyl group, a propoxycarbonyl group, a butoxycarbonyl group and the like. A methoxycarbonyl group, an ethoxycarbonyl group and a propoxycarbonyl group are more preferred; a methoxycarbonyl group and an ethoxycarbonyl group are even more preferred; and a methoxycarbonyl group is particularly preferred. A combination of a lower alkoxycarbonyl group and a hydrogen atom, particularly a combination of a methoxycarbonyl group and a hydrogen atom are preferred as the combination of $R_5$ and $R_6$.

At least one of $R_5$ and $R_6$ is preferably a lower alkenyl group, and the lower alkenyl group may be exemplified by a lower alkenyl group having 2 to 10 carbon atoms, preferably 2 to 5 carbon atoms, more preferably 2 to 3 carbon atoms, and particularly preferably 2 carbon atoms. A combination of a lower alkenyl group and a hydrogen atom, particularly a combination of a vinyl group and a hydrogen atom are preferred as the combination of $R_5$ and $R_6$.

At least one of $R_5$ and $R_6$ is preferably a lower alkynyl group, and the lower alkynyl group may be exemplified by a lower alkynyl group having 2 to 10 carbon atoms, preferably 2 to 5 carbon atoms, more preferably 2 to 3 carbon atoms, and particularly preferably 2 carbon atoms. A combination of a lower alknyl group and a hydrogen atom, particularly a combination of an ethynyl group and a hydrogen atom are preferred as the combination of $R_5$ and $R_6$.

At least one of $R_5$ and $R_6$ is preferably substituted amide, and the substituted amide may be exemplified by monosubstituted, N-substituted amide. Preferred examples thereof include N-alkylamide and N-aminoalkylamide. Such N-alkylamide or N-aminoalkylamide is preferably a compound having 1 to 10 carbon atoms, preferably 1 to 5 carbon atoms, more preferably 1 to 3 carbon atoms, and particularly preferably 3 carbon atoms, and N-aminoalkylamide is particularly preferred. A combination of substituted amide and a hydrogen atom, particularly a combination of N-amino($C_1$-$C_3$ alkyl)amide and a hydrogen atom are preferred as the combination of $R_5$ and $R_6$.

At least one of $R_5$ and $R_6$ is preferably an amide group, and a combination of an amide group and a hydrogen atom is preferred as the combination of $R_5$ and $R_6$.

At least one of $R_5$ and $R_6$ is preferably a cyano group, and a combination of a cyano group and a cyano group, and a combination of a cyano group and a hydrogen atom are preferred as the combination of $R_5$ and $R_6$.

At least one of $R_5$ and $R_6$ is preferably a hydrogen atom, and a combination including at least one hydrogen atom, and a combination of a hydrogen atom and a hydrogen atom are preferred as the combination of $R_5$ and $R_6$.

In another preferred embodiment, the photoligating nucleic acid has a group represented by the following Formula IV:

[Formula IV]

[Chemical Formula 9]

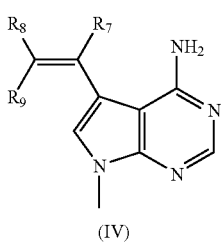

(IV)

wherein $R_7$ is a hydrogen atom or a lower alkyl group; at least one of $R_8$ and $R_9$ represents a group selected from the group consisting of a carboxyl group, a lower alkoxycarbonyl group, a lower alkenyl group, a lower alkynyl group, a substituted amide group, an amide group, a cyano group and a hydrogen atom; and the residue of $R_8$ and $R_9$ represents a hydrogen atom or a cyano group; as a base moiety.

$R_7$ is particularly preferably a hydrogen atom.

$R_7$ is preferably a lower alkyl group, and the lower alkyl group is a group having 1 to 5 carbon atoms, preferably 1 to 3 carbon atoms, more preferably 1 to 2 carbon atoms, and particularly preferably one carbon atom. Such lower alkyl group may be exemplified by a methyl group, an ethyl group, a propyl group or the like, and a methyl group and an ethyl group are preferred, while a methyl group is particularly preferred.

At least one of $R_8$ and $R_9$ is preferably a carboxyl group, and a combination of a carboxyl group and a hydrogen atom is preferred as the combination of $R_8$ and $R_9$.

At least one of $R_8$ and $R_9$ is preferably a lower alkoxycarbonyl group, and the alkyl moiety in the lower alkoxycarbonyl group may be exemplified by lower alkyl having 1 to 10 carbon atoms, preferably 1 to 5 carbon atoms, more preferably 1 to 3 carbon atoms, even more preferably 1 to 2 carbon atoms, and particularly preferably one carbon atom. That is, preferred examples of the lower alkoxycarbonyl group include a methoxycarbonyl group, an ethoxycarbonyl group, a propoxycarbonyl group, a butoxycarbonyl group and the like. A methoxycarbonyl group, an ethoxycarbonyl group and a propoxycarbonyl group are more preferred; a methoxycarbonyl group and an ethoxycarbonyl group are even more preferred; and a methoxycarbonyl group is particularly preferred. A combination of a lower alkoxycarbonyl group and a hydrogen atom, particularly a combination of a methoxycarbonyl group and a hydrogen atom are preferred as the combination of $R_8$ and $R_9$.

At least one of $R_8$ and $R_9$ is preferably a lower alkenyl group, and the lower alkenyl group may be exemplified by a lower alkenyl group having 2 to 10 carbon atoms, preferably 2 to 5 carbon atoms, more preferably 2 to 3 carbon atoms, and particularly preferably 2 carbon atoms. A combination of a lower alkenyl group and a hydrogen atom, particularly a combination of a vinyl group and a hydrogen atom are preferred as the combination of $R_8$ and $R_9$.

At least one of $R_8$ and $R_9$ is preferably a lower alkynyl group, and the lower alkynyl group may be exemplified by a lower alkynyl group having 2 to 10 carbon atoms, preferably 2 to 5 carbon atoms, more preferably 2 to 3 carbon atoms, and particularly preferably 2 carbon atoms. A combination of a lower alkynyl group and a hydrogen atom, particularly a combination of an ethynyl group and a hydrogen atom are preferred as the combination of $R_8$ and $R_9$.

At least one of $R_8$ and $R_9$ is preferably substituted amide, and the substituted amide may be exemplified by monosubstituted, N-substituted amide. Preferred examples thereof include N-alkylamide and N-aminoalkylamide. Such N-alkylamide or N-aminoalkylamide is preferably a compound having 1 to 10 carbon atoms, preferably 1 to 5 carbon atoms, more preferably 1 to 3 carbon atoms, and particularly preferably 3 carbon atoms, and N-aminoalkylamide is particularly preferred. A combination of substituted amide and a hydrogen atom, particularly a combination of N-amino($C_1$-$C_3$ alkyl)amide and a hydrogen atom are preferred as the combination of $R_8$ and $R_9$.

At least one of $R_8$ and $R_9$ is preferably an amide group, and a combination of an amide group and a hydrogen atom is preferred as the combination of $R_8$ and $R_9$.

At least one of $R_8$ and $R_9$ is preferably a cyano group, and a combination of a cyano group and a cyano group, and a combination of a cyano group and a hydrogen atom are preferred as the combination of $R_8$ and $R_9$.

At least one of $R_8$ and $R_9$ is preferably a hydrogen atom, and a combination including at least one hydrogen atom, and a combination of a hydrogen atom and a hydrogen atom are preferred as the combination of $R_8$ and $R_9$.

In another preferred embodiment, the photoligating nucleic acid has a group represented by the following Formula V:

[Formula V]

[Chemical Formula 10]

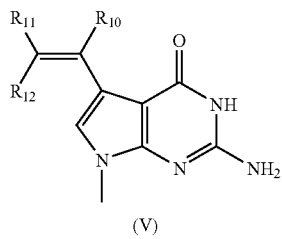

(V)

wherein $R_{10}$ is a hydrogen atom or a lower alkyl group; at least one of $R_{11}$ and $R_{12}$ represents a group selected from the group consisting of a carboxyl group, a lower alkoxycarbonyl group, a lower alkenyl group, a lower alkynyl group, a substituted amide group, an amide group, a cyano group and a hydrogen atom; and the residue of $R_{11}$ and $R_{12}$ represents a hydrogen atom or a cyano group; as a base moiety.

$R_{10}$ is particularly preferably a hydrogen atom.

$R_{10}$ is preferably a lower alkyl group, and the lower alkyl group is a group having 1 to 5 carbon atoms, preferably 1 to 3 carbon atoms, more preferably 1 to 2 carbon atoms, and particularly preferably one carbon atom. Such lower alkyl group may be exemplified by a methyl group, an ethyl group, a propyl group or the like, and a methyl group and an ethyl group are preferred, while a methyl group is particularly preferred.

At least one of $R_{11}$ and $R_{12}$ is preferably a carboxyl group, and a combination of a carboxyl group and a hydrogen atom is preferred as the combination of $R_{11}$ and $R_{12}$.

At least one of $R_{11}$ and $R_{12}$ is preferably a lower alkoxycarbonyl group, and the alkyl moiety in the lower alkoxycarbonyl group may be exemplified by lower alkyl having 1 to 10 carbon atoms, preferably 1 to 5 carbon atoms, more preferably 1 to 3 carbon atoms, even more preferably 1 to 2 carbon atoms, and particularly preferably one carbon atom. That is, preferred examples of the lower alkoxycarbonyl group include a methoxycarbonyl group, an ethoxycarbonyl group, a propoxycarbonyl group, a butoxycarbonyl group and the like. A methoxycarbonyl group, an ethoxycarbonyl group and a propoxycarbonyl group are more preferred; a methoxycarbonyl group and an ethoxycarbonyl group are even more preferred; and a methoxycarbonyl group is particularly preferred. A combination of a lower alkoxycarbonyl group and a hydrogen atom, particularly a combination of a methoxycarbonyl group and a hydrogen atom are preferred as the combination of $R_{11}$ and $R_{12}$.

At least one of $R_{11}$ and $R_{12}$ is preferably a lower alkenyl group, and the lower alkenyl group may be exemplified by a lower alkenyl group having 2 to 10 carbon atoms, preferably 2 to 5 carbon atoms, more preferably 2 to 3 carbon atoms, and particularly preferably 2 carbon atoms. A combination of a lower alkenyl group and a hydrogen atom, particularly a combination of a vinyl group and a hydrogen atom are preferred as the combination of $R_{11}$ and $R_{12}$.

At least one of $R_{11}$ and $R_{12}$ is preferably a lower alkynyl group, and the lower alkynyl group may be exemplified by a lower alkynyl group having 2 to 10 carbon atoms, preferably 2 to 5 carbon atoms, more preferably 2 to 3 carbon atoms, and particularly preferably 2 carbon atoms. A combination of a lower alkynyl group and a hydrogen atom, particularly a combination of an ethynyl group and a hydrogen atom are preferred as the combination of $R_{11}$ and $R_{12}$.

At least one of $R_{11}$ and $R_{12}$ is preferably substituted amide, and the substituted amide may be exemplified by mono-substituted, N-substituted amide. Preferred examples thereof include N-alkylamide and N-aminoalkylamide. Such N-alkylamide or N-aminoalkylamide is preferably a compound having 1 to 10 carbon atoms, preferably 1 to 5 carbon atoms, more preferably 1 to 3 carbon atoms, and particularly preferably 3 carbon atoms, and N-aminoalkylamide is particularly preferred. A combination of substituted amide and a hydrogen atom, and particularly a combination of N-amino($C_1$-$C_3$ alkyl)amide and a hydrogen atom, are preferred as the combination of $R_{11}$ and $R_{12}$.

At least one of $R_{11}$ and $R_{12}$ is preferably an amide group, and a combination of an amide group and a hydrogen atom is preferred as the combination of $R_{11}$ and $R_{12}$.

At least one of $R_{11}$ and $R_{12}$ is preferably a cyano group, and a combination of a cyano group and a cyano group, and a combination of a cyano group and a hydrogen atom are preferred as the combination of $R_{11}$ and $R_{12}$.

At least one of $R_{11}$ and $R_{12}$ is preferably a hydrogen atom, and a combination including at least one hydrogen atom, and a combination of a hydrogen atom and a hydrogen atom are preferred as the combination of $R_{11}$ and $R_{12}$.

Suitable structural formulae of such base are illustrated as the following. However, the base that can be used in the present invention is not limited to the following examples.

[Chemical Formula 11]

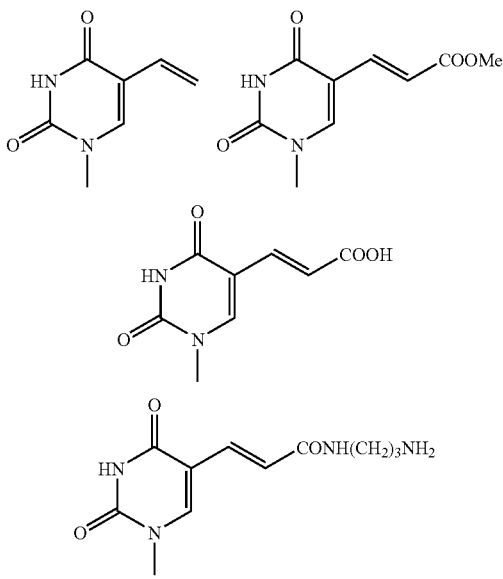

-continued

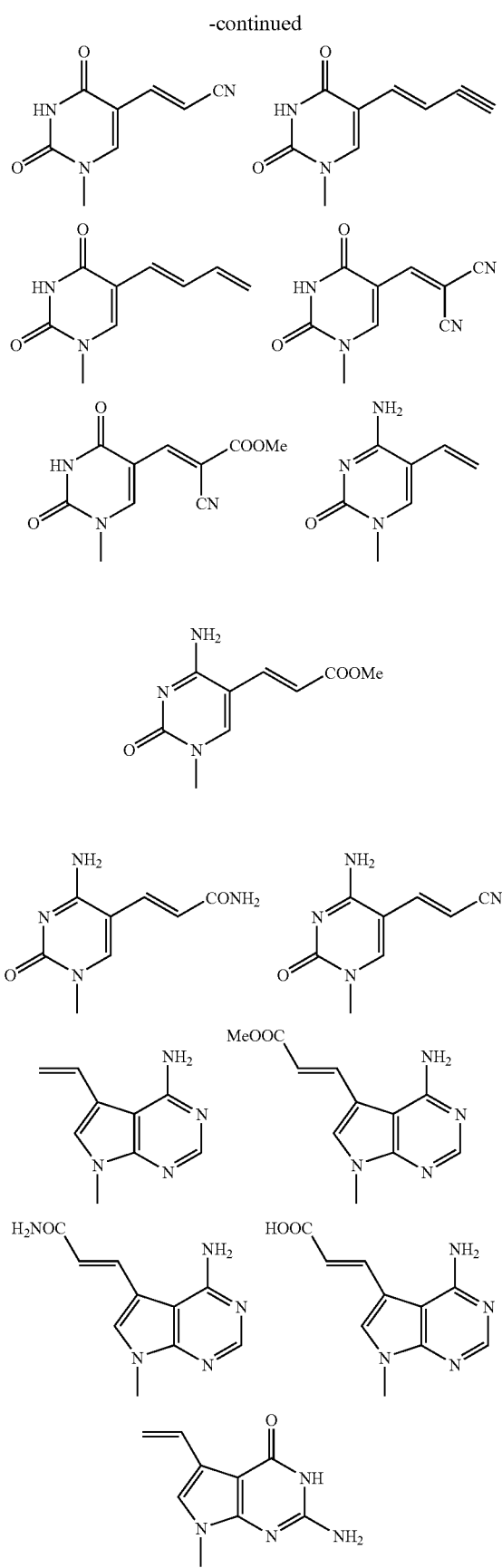

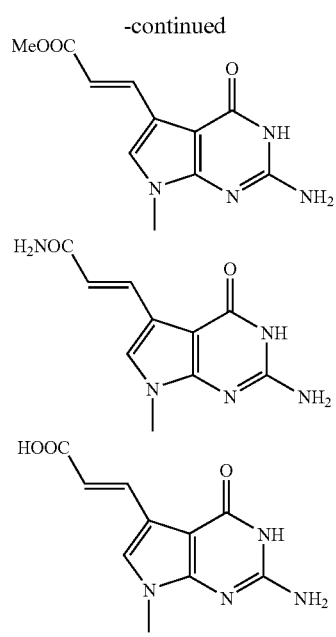

The photoligating nucleic acid has a group represented by the Formula I as the base moiety at the 5'-end or the 3'-end. In this case, the photoligated nucleic acid has, in response to the above, a base having a carbon-carbon double bond as a base moiety capable of being photoligated at the 3'-end or the 5'-end, so that the photoligated nucleic acid can be photoligated to the photoligating nucleic acid.

The nucleic acid of the photoligating nucleic acid includes a nucleic acid and a peptide nucleic acid (PNA). The nucleic acid includes a DNA and an RNA, and an oligonucleotide other than these. These may be either naturally occurring or synthetic. Any nucleic acid capable of forming complementary double strands resulting from hybridization according to the present invention can be used.

The photoligating nucleic acid can be produced according to a conventional method for producing nucleic acid. For example, a DMTr-derivative of 5-substituted vinyluridine is subjected to an amididating agent to amididate the derivative, subsequently the protective group is cleaved, and the resultant can be converted to an oligonucleotide by a conventional DNA synthesis method. A 5-substituted vinylcytosine derivative or a 5-substituted vinyluracil derivative can be produced according to the method of the following specific example, but can also be produced according to some other conventional organic synthesis method.

The photoligated nucleic acid has a base having a carbon-carbon double bond as a base moiety capable of being photoligated to the photoligating nucleic acid at the 3'-end and the 5'-end. For the base having a carbon-carbon double bond, a carbon-carbon double bond forming a fused ring is not preferred, while a monocyclic carbon-carbon double bond or a carbon-carbon double bond substituted on a ring is preferred. A preferred base having a carbon-carbon double bond may be exemplified by naturally occurring substances such as cytosine, thymine and uracil.

The nucleic acid of the photoligated nucleic acid includes a nucleic acid and a peptide nucleic acid (PNA). The nucleic acid includes a DNA and an RNA, and an oligonucleotide other than these. These may be either naturally occurring or synthetic. Any nucleic acid capable of forming complementary double strands resulting from hybridization according to the present invention can be used.

The nucleic acid of the photoligated nucleic acid can be produced according to a conventional method for producing nucleic acid, as in the case of photoligating nucleic acid.

The photoligating nucleic acid and the photoligated nucleic acid may be nucleic acids of the same kind, or may be nucleic acids of different kinds.

Either one of the photoligating nucleic acid and the photoligated nucleic acid has a labeling moiety, and the one not having a labeling moiety between the photoligating nucleic acid and the photoligated nucleic acid is immobilized on a substrate in advance.

Various labels can be used as the label of the labeling moiety, and for example, biotin labels, dye labels (including fluorescent dye labels), RI labels, and enzyme labels (including chromogenic enzyme labels) can be used. A label which can endure the washing under the rigorous washing condition that is made possible in the present invention is preferred. From the viewpoint of ease of handling and resistance to rigorous washing condition, a biotin label or a fluorescent dye label is preferred. The biotin label can be detected using various other labels having an avidin moiety, on the basis of the biotin-avidin bonding. Addition of these labeling moieties can be performed according to conventional production methods. Typically, it is preferable for the photoligating nucleic acid and the photoligated nucleic acid to have labeling moieties near the end that is not subject to photoligation, but may also have labeling moieties in any other areas, within the scope of not adversely affecting the photoligation and hybridization.

As for the substrate on which the photoligating nucleic acid or the photoligated nucleic acid is immobilized, various forms such as beads and plates can be used, but it is preferable to use a plate-shaped substrate for suitable use on DNA chips (DNA microarrays) or the like.

As for the material of the substrate, materials of various textures which are likely to be used as solid carriers in the biochemistry field can be used. For example, there may be mentioned inorganic materials such as glass and porous glass; resins such as polystyrene (PS); metals such as gold, and the like. Preferred materials include solid carrier having an adenosine residue (Oligo Affinity Support (OAS), etc.), aldehyde-modified glass, and the like. A glass plate, CPG, polystyrene beads and the like are preferred. Conventional materials used as the substrate of DNA chips can be suitably used.

Either one of the photoligating nucleic acid and the photoligated nucleic acid which is immobilized on the substrate in advance may be immobilized by directly binding to the substrate, but in order to form a good hybrid, it is preferable to immobilize the nucleic acid on the substrate via a linker moiety. The linker moiety may be a molecule species having 5 or more atoms, preferably 10 or more atoms which is inert to the chemical reactions of nucleic acid, and preferably straight-chained. The linker moiety is preferably a nucleic acid such as DNA, RNA or PNA, polyethylene glycol, an alkane or the like. Polyethylene glycol is particularly preferred, and hexa(ethylene glycol) can be suitably used. As for the method for producing a nucleic acid immobilized on a substrate, production can be carried out by binding the phosphoric acid group present at the end of the nucleic acid, to the linker moiety. The binding process may be carried out such that the linker moiety and the nucleic acid are bound, and then the resultant is bound to the substrate. On the contrary, the substrate and the linker moiety may be first bound, and then the linker moiety and the nucleic acid may be bound. As for the position for binding to the nucleic acid, it is usually preferable to use the phosphoric acid group at the end, but the position is not limited thereto. For example, the linker moiety may be bound to the functional group of the base moiety in the middle of the nucleic acid.

The photoligating nucleic acid and the photoligated nucleic acid are produced so as to generate a nucleic acid having a base sequence that is complementary to the base sequence of the target nucleic acid having a specific base sequence through photoligation. The photoligating nucleic acid and the photoligated nucleic acid are adjacently arranged to enable photoligation, by performing hybridization using the target nucleic acid as the template.

This hybridization can be performed under usual conditions of temperature, pH, salt concentration, buffering solution and the like. However, it is an advantage of the present invention that detection can be achieved with higher specificity and sensitivity (S/N ratio), by making it possible to select the conditions for hybridization and photoligation with a high degree of freedom. As these conditions, for example, temperature, the type and concentration of solvent (solute), salt or the like may be mentioned.

Among the conditions for hybridization, the temperature in the present invention can be any temperature which allows hybridization to occur, but it was found that in order to perform the processes of hybridization and photoligation very rapidly, it is preferable to perform the processes at a temperature of 20° C. to 30° C., and particularly at room temperature.

Furthermore, it is preferable to perform hybridization in a reaction solution containing a salt having buffering effects. It is preferable that pH of the reaction solution is in the range of 6.5 to 8.5, and particularly in the range of 6.7 to 7.7. The concentration of the salt having buffering effects is preferably in the range of 5 to 250 mM, and particularly preferably in the range of 10 to 100 mM. As the salt having buffering effects, cacodylates, phosphates, tris-salts and the like may be mentioned, but in the present invention, particularly from the viewpoint of increasing the fluorescence intensity, the salt having buffering effects is preferably a cacodylate. It has been found that with the use of a cacodylate under the above-mentioned conditions, the fluorescence intensity can be increased to approximately 10 times the fluorescence intensity obtained using a PBS buffer solution or the like. It has been also found that the reaction solution preferably contains a water-dispersible organic solvent, and particularly from the viewpoint of the rapidness of reaction, the reaction solution preferably contains 20% to 60% (by volume) of a water-dispersible organic solvent. In particular, this water-dispersible organic solvent is preferably acetonitrile. It was also found in the present invention that the reaction solution preferably contains a salt of an alkali metal and/or alkaline earth metal, and in order to achieve a high S/N ratio, the concentration of the salt has an optimum value for the respective concentrations of the target nucleic acid. That is, it is preferable that these reaction solutions are optimized with respect to these two conditions through an examination of conditions. As the salt of an alkali metal and/or alkaline earth metal, it is preferable to contain, for example, sodium chloride and/or magnesium chloride.

Photoligation of the photoligating nucleic acid and the photoligated nucleic acid is conducted by a photochemical reaction involving photoirradiation. The light for irradiation may include a wavelength having the energy needed in the reaction, and ultraviolet light is preferred. The wavelength preferably includes 330 nm or longer, preferably 350 nm or longer, and more preferably 360 nm or longer. As a particularly preferred wavelength, 366 nm may be mentioned.

Moreover, this photoligation has reversibility in its principle. Therefore, it is possible to cause cleavage by irradiating a light with a relatively short wavelength. The wavelength at the time of cleavage, a wavelength of 320 nm or shorter, and preferably 310 nm or shorter is preferred. As a particularly preferred wavelength in the cleavage, 302 nm may be mentioned. Although not shown in FIG. 1, it is also possible to detect the labeling moiety in a solution detached from the substrate after further carrying out the process of cleaving the photoligated nucleic acid. When such process is further carried out, various detection methods can be used while making the best use of the high specificity and sensitivity of the present invention. The inventors of the present invention have already filed a patent application on the principle of this photoligation, and the subject matters of Japanese Patent Application No. 2000-67519, Japanese Patent Application No. 2000-256068, Japanese Patent Application No. 2000-382283 and Japanese Patent Application No. 2001-750 can be incorporated into the present invention.

After the labeling moiety has been immobilized on the substrate through photoligation, washing is performed under a washing condition that would dissociate complementary double strands resulting from hybridization.

Unless the labeling moiety immobilized on the substrate is subjected to a condition that is likely to cause detachment due to the destruction of covalent bonding in the middle, the labeling moiety can be subjected to a condition where however strong the effect of dissociating complementary double strands is. In order to completely remove a labeling moiety that is likely to be weakly bound to the substrate by incomplete hybridization without being photoligated because of imperfect complementarity, it is desirable that the washing condition induces strong dissociation effects of complementary double strands.

As for suitable washing conditions, for example, a temperature in the range of 80° C. to 100° C., preferably 90° C. to 100° C., particularly preferably 95° C. to 100° C. can be used. The temperature may range from the value of boiling point to a value as high as achievable as long as the temperature does not cause decomposition of covalent bonding. pH is not particularly limited as long as the pH does not cause decomposition of covalent bonding, but the value is preferably near neutrality because hydrolysis of covalent bonding is difficult to occur. The type of salt and the salt concentration are not particularly limited as long as inadequate precipitates of a sample are not generated in the operation, and the presence of a salt at a generally suitable concentration (for example, about 0.1 M NaCl) is adequate for accelerating dissociation of complementary double strands. Further, in order to accelerate dissociation of complementary double strands, for example, urea can be added as a denaturing agent. Also, for example, sodium dodecyl sulfate can be added as a surfactant in order to accelerate dissociation of complementary double strands. In addition to these, the conditions known to be contributive to dissociation of complementary double strands can be used.

The detection of labeling moiety that is performed after the washing can be carried out using a conventional method corresponding to the respective principles of the label. For example, for an RI label, autoradiography can be performed, while for a fluorescent dye label, reading from a laser scanner can be used. Also, for a biotin label, a separate label having avidin is provided to bring a new label involving avidin-biotin bonding, and then a conventional method corresponding to the principle of the label can be used.

Although discussion was given on embodiments for immobilizing the labeling moiety by utilizing photoligation only once, embodiments for immobilizing the labeling moiety by utilizing photoligation several times (a set of nucleic acids used in those embodiments, and a detection method according thereto) are also included in the scope of the present invention. For example, an embodiment in which one or more fragments of nucleic acid are linked between the nucleic acid having a labeling moiety and the nucleic acid immobilized on a substrate through hybridization and photoligation is also possible according to the present invention.

Implementation of the present invention will be described in detail as the following by way of Examples. In particular, experimental operations without any specifying description were carried out under the conventional conditions employed by an ordinarily skilled person (for example, atmospheric pressure and room temperature).

EXAMPLES

Example 1

An experiment targeted to an RNA was performed as follows.

[Synthesis of Photoligating Oligonucleotide]

An ODN containing 5-carboxyvinyl-2'-deoxyuridine ($^{CV}$U), i.e., ODN1($^{CV}$U)5'-d($^{CV}$UGCGTG)-3', was synthesized by a conventional DNA synthesis method using cyanoethylphosphoramidite of CVU. ODN1($^{CV}$U) was identified by means of nucleotide composition and MALDI-TOF-MS (calcd. 1876.3381 for [M–H]–; found 1876.3477).

[RNA template-directed photoligation involving ODN1 (CVU)]

The feasibility of RNA template-directed photoligation involving ODN1(CVU) was confirmed as follows. When ODN1(CVU) and ODN(T)5'-d(TGTGCT)-3' were irradiated with light at 366 nm for 30 minutes in the presence of RNA (A)5'-r(CACGCAAGCACA)-3' (SEQ ID NO: 1) (FIG. 2), it was confirmed by HPLC that a peak for ODN(CVU-T) appears at a yield of 98% with the disappearance of the peaks for ODN(CVU) and ODN(T) (FIG. 3). MALDI-TOF-MS showed that the isolated ODN(CVU-T) obtained by HPLC purification was a photoligation product of ODN(CVU) and ODN(T) (calcd. 3677.51 for [M+H]+; found 3677.82). When ODN(CVU) and ODN(T) were irradiated with light at 366 nm for 30 minutes in the presence of ODN(A)5'-d(CACG-CAAGCACA)-3' (SEQ ID NO: 2), it was confirmed by HPLC that a peak for ODN(CVU-T) appeared at a yield of 74%. Meanwhile, when an RNA template is used in the photoligation, C at the 3'-end reacts with photoexcited CVU to produce photoligated ODN(CVU-C) with an efficiency as good as that in the case of T at the 3'-end.

[Confirmation of Photoreversibility]

In order to confirm the photoreversibility of the ligated product, a test was performed by irradiating photoligated ODN($^{CV}$U-T) with light at 312 nm. When isolated ODN ($^{CV}$U-T) was irradiated with light at 312 nm for 4 minutes, appearance of the peaks for OND1 ($^{CV}$U) and ODN(T) with a yield of 49% was confirmed by HPLC, along with the disappearance of the peak for ODN($^{CV}$U-T). Therefore, ODN containing $^{CV}$U at the 5'-end has photoreversibility.

[Detection of RNA Point Mutation]

Figure 1:
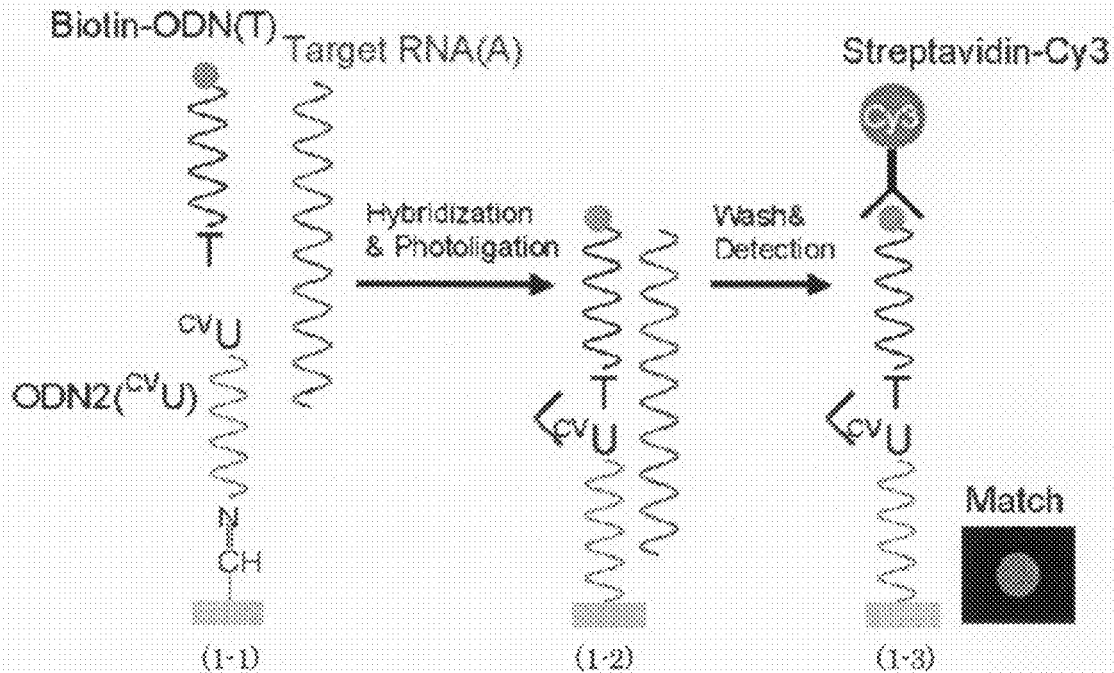
FIG. 1 is an explanatory diagram showing the flow of an embodiment of the present invention.

For the detection of RNA point mutation, template-directed photoligation of ODN covalently arranged on a DNA chip was used (FIG. 1). In order to prove that RNA template-directed photoligation can be utilized through incorporation into a platform appropriate for the DNA chip technology, a DNA chip was constructed by adding an amino-labeled ODN containing $^{CV}$U, i.e., ODN2($^{CV}$U)5'-d($^{CV}$UGCGTG)-SSSS-NH$_2$-3' (wherein S corresponds to a hexa(ethylene glycol) linker fragment) to an aldehyde-modified glass surface.

Figure 4:
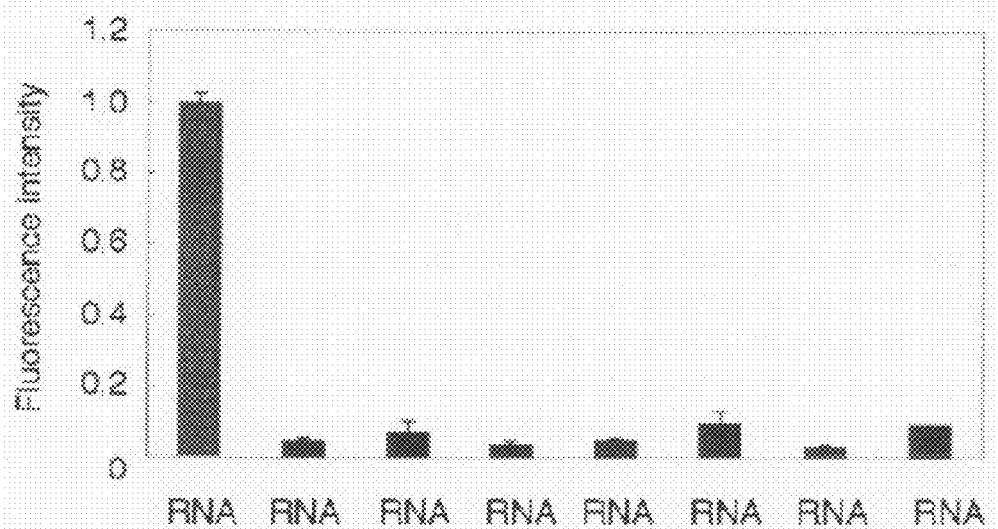
FIG. 4 shows the results of the detection of a point mutation of RNA according to the present invention.

The applicability of RNA template-directed photoligation was confirmed using ODN2($^{CV}$U) on a DNA chip. A 2 μM target RNA(A) and a biotin-labeled ODN(T), i.e., 5'-biotin-TGTGC T-3' were spotted, and were irradiated with light at 366 nm for 10 minutes in a 50 mM sodium cacodylate buffer solution (pH 7.0) and 100 mM sodium chloride. The chip was washed with deionized water at 98° C. for 5 minutes, subsequently a PBS solution of streptoavidin-Cy3-conjugate was added to the surface, and the chip was washed two times with PBS buffer solution. The fluorescence signals were detected using a microarray scanner. As shown in FIG. 4, when a perfectly complementary strand was formed, an intense fluorescent signal of the photoligation product was detected. To confirm the generality of sequence discrimination, five target RNAs having mismatches at various positions were constructed. As a result, in the case of RNA, a single mismatch at the 9$^{th}$ position hardly produces a photoligation product, and the intensity of the measured fluorescence signal was 1/33 of the signal intensity obtained in the case of having perfect complementarity (Table 1). Subsequently, a set of four very similar target RNAs respectively having a single base altered (A, U, G or C) at the 9$^{th}$ position were constructed. Most of the mismatches induced fluorescence signals with relatively smaller intensities by 10% or more, compared to the case of correct matches.

From the above, RNA template-directed fluorescence photoligation involving $^{CV}$U was proved. When an ODN containing $^{CV}$U at the 5'-end was photoirradiated together with an ODN containing pyrimidine base at the 3'-end in the presence of a template RNA, efficient photoligation was occurred without formation of side products. Moreover, mismatches at various positions can be well distinguished by utilizing DNA chip analysis based on RNA template-directed photoligation. Therefore, this system can be widely used for specific detection of RNA sequence.

[Detection of Photoligation of ODN by HPLC]

A reaction mixture (total volume of 60 μL) containing ODN1($^{CV}$U) and ODN(T) (20 μM each, strand concentration) was irradiated with a 25-W transilluminator (366 nm) at 0° C. for 30 minutes in a 50 mM sodium cacodylate buffer solution (pH 7.0) and 100 mM sodium chloride in the presence of template RNA(A) (24 μM, strand concentration). After the irradiation, the progress of the photoreaction was detected by HPLC using a Cosmosil 5C18AR column (4.6× 150 mm, pH 7.0, a linear gradient of 6% to 10% acetonitrile for 30 minutes flow rate 0.5 mL/min, elution with a 50 mM ammonium formate-solvent mixture).

[Preparation of Oligonucleotide]

An ODN was synthesized according to a conventional phosphoramidite method using an Applied Biosystems 3400 DNA synthesis apparatus. The binding efficiency was monitored with a trityl monitor. The binding efficiency of cyanoethylphosphoramidite of $^{CV}$U was 97% yield. The binding time of cyanoethylphosphoramidite of $^{CV}$U was 999 seconds. These were deprotected by maintaining them in 28% ammonia at 65° C. for 4 hours, and purified by reverse phase HPLC using a Chemcobond 5-ODS-H column (4.6×150 mm); and elution was performed with 0.05 M ammonium formate containing 3% to 20% acetonitrile, with a linear gradient (for 30 minutes), at a flow rate of 1.0 mL/min and at 30° C. Purification of the oligonucleotide was confirmed by MALDI-TOF-MS analysis.

[Monitoring of Photocleavage of Photoligation Product by HPLC]

Figure 5:
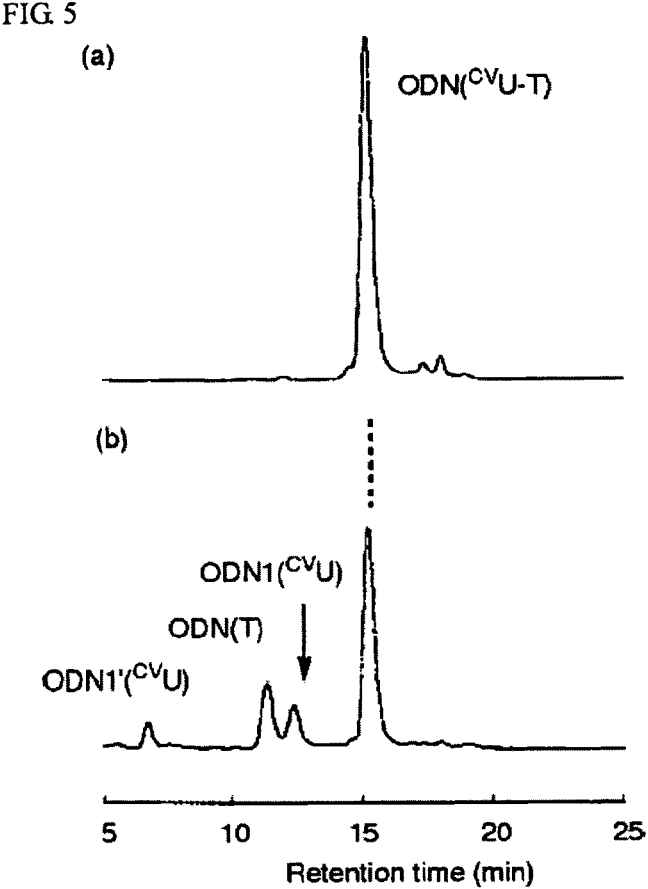
FIG. 5 is an HPLC chart showing reversibility of the photoligation of nucleic acids.

A 50 mM sodium cacodylate buffer solution (pH 7.0) containing photoligated ODN ($^{CV}$U-T) (20 µM, strand concentration) and a solution of 100 mM sodium chloride (total volume of 60 µL) were irradiated with a 15-W transilluminator (312 nm) at 25° C. for 4 minutes. After the irradiation, progress of the photoreaction was monitored by HPLC using a Cosmosil 5C18AR column (4.6×150 mm, elution with a 50 mM ammonium formate-solvent mixture, a 6% to 12% acetonitrile linear gradient for 30 minutes at a flow rate of 0.8 mL/min) (FIG. 5). ODN1'($^{CV}$U) was a cis-isomer of ODN1 ($^{CV}$U).

Figure 6:
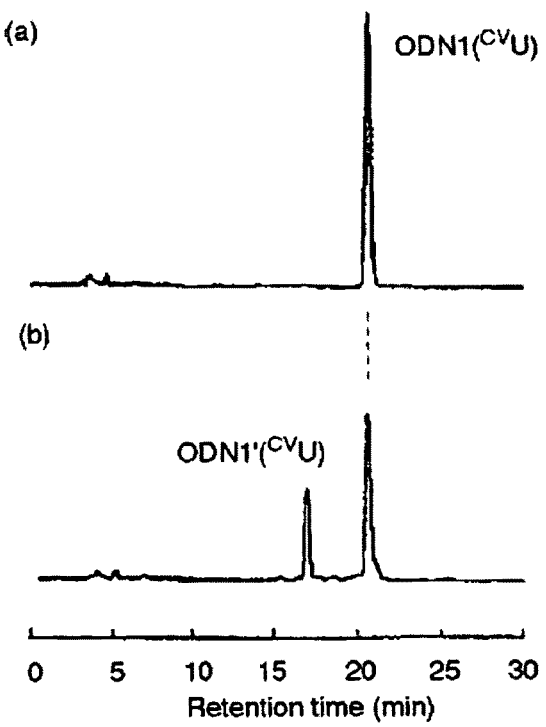
FIG. 6 is an HPLC chart showing reversibility of the photoligation of nucleic acids.

A 50 mM sodium cacodylate buffer solution (pH 7.0) containing photoligated ODN($^{CV}$U) (20 µM, strand concentration) and a 100 mM solution of sodium chloride (total volume of 60 µL) were irradiated with a 15-W transilluminator (312 nm) at 25° C. for 2 minutes. After the irradiation, progress of the photoreaction was monitored by HPLC using a Cosmosil 5C18AR column (4.6×150 mm, elution with a 50 mM ammonium formate-solvent mixture, a 6% to 11% acetonitrile linear gradient for 30 minutes at a flow rate of 0.5 mL/min) (FIG. 6).

[Immobilization of DNA Probe]

An amino-labeled ODN probe containing $^{CV}$U was diluted with a 100 mM sodium cacodylate buffer solution (pH 7.0) to a concentration of 2×10$^5$ M. Spotting was performed using 5 µL each from a standard micropipette. Binding of amino-labeled ODN probe containing $^{CV}$U to the surface was conducted over a period of 12 hours at room temperature inside a desiccator. After the immobilization of probe, the glass surface was washed with 0.1% SDS and deionized water. This surface was made inert with a solution of NaBH$_4$ (3.75 mg), PBS (1.5 mL) and ethanol (375 µL) for 5 minutes. Subsequently, this surface was washed with deionized water, and dried.

[RNA Template-Directed Photoligation on DNA Chip]

Figure 7:
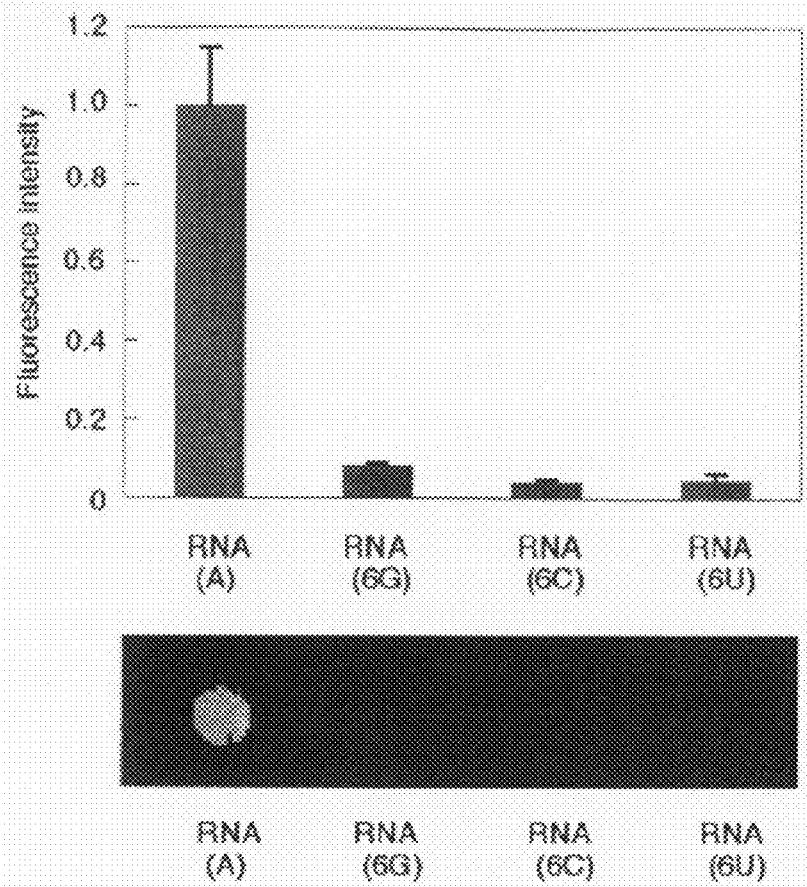
FIG. 7 shows the results of the detection of a point mutation of RNA according to the present invention.

A glass chip spotted with a solution (5 µL) of 2 µM target RNA(A) and biotin-labeled ODN(T) in 50 mM sodium cacodylate buffer solution (pH 7.0) and 100 mM sodium chloride, was irradiated with light at 366 nm for 10 minutes. The chip was washed with deionized water at 98° C. for 5 minutes, subsequently a PBS solution of streptavidin-Cy3-conjugate (20 µg/mL) was added to the surface, and the chip was washed two times with PBS buffer solution. Fluorescence measurement was performed using a microarray scanner CRBIO IIe (Hitachi) equipped with a laser at an excitation wavelength of 532 nm. Subsequently, a set of four closely related target RNAs respectively having a single base altered (A, U, G or C) at the 6$^{th}$ position was constructed (Table 2). In most of the mismatches, the intensity of the relative fluorescence signal was decreased by 8% or more, compared to the case of correct mismatches (FIG. 7).

Example 2

An experiment targeted to DNA was performed as follows.

[Immobilization of Probe ODN]

A probe ODN having amine terminals and a photoresponsive base was immobilized to an aldehyde-treated microarray slide (manufactured by Nunc, Inc.) according to the following procedure.

1. The probe ODN was adjusted to a concentration of 0.2 µg/µl in a buffer solution (sodium phosphate buffer solution pH 8.5, 0.01% SDS).
2. 10 µl of this solution was added dropwise, and dried for 24 hours at room temperature to immobilize the probe ODN.
3. After the immobilization, the probe ODN was washed two times with 0.15% SDS, and two times with ultrapure water.
4. A PBS/ethanol solution of NaBH$_4$ was added dropwise.
5. The probe ODN was washed with ultrapure water.

Through this procedure, the probe ODN could be immobilized at a density of 1.5 to 1.8×10$^{11}$/cm$^2$.

[Photoligation on DNA Chip]

Figure 8:
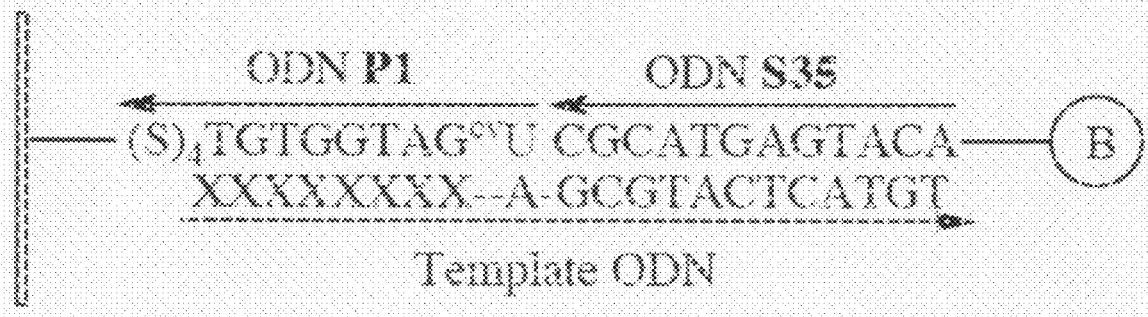
FIG. 8 is an explanatory diagram showing another embodiment of the present invention.

Photoligation on a DNA chip was carried out to achieve the embodiment as shown in FIG. 8. ODN P1 is an oligonucleotide immobilized on a substrate via hexa(ethylene glycol (S), and has a photoligating base moiety ($^{CV}$U). ODN S35 is an oligonucleotide having biotin (B) at the end as a labeling moiety and has a photoligated base moiety (C in the drawing). In FIG. 8, this ODN P1 and ODN S35 are arranged adjacently to each other in a state where photoligation can be achieved through hybridization using a target oligonucleotide (Template ODN) as the template. Photoligation takes place when photoirradiation is performed in this state. The experiment was performed such that hybridization was achieved at room temperature under the conditions of ODN S35 (2 µM), template-ODN (2 µM), sodium cacodylate (50 mM) and NaCl (25 mM). Photoligation was achieved by irradiating the system with light at a wavelength of 366 nm for 10 minutes.

With regard to the XX to XX moiety of the template ODN, such photoligation was carried out for 33 sequences resulting from a single base substitution, a two-base substitution or a three-base substitution from a complementary sequence corresponding to ODN P1, to conduct the detection of a labeled moiety. It was found that perfectly complementary sequences could be identified with very high specificity and sensitivity (S/N ratio).

Furthermore, the optimum temperature was searched by changing the temperature of this hybridization to 0° C., 10° C. or room temperature, and it was found that room temperature is most suitable.

[Detection of Genetic Polymorphism (SNPs) on DNA Chip]

Figure 9:
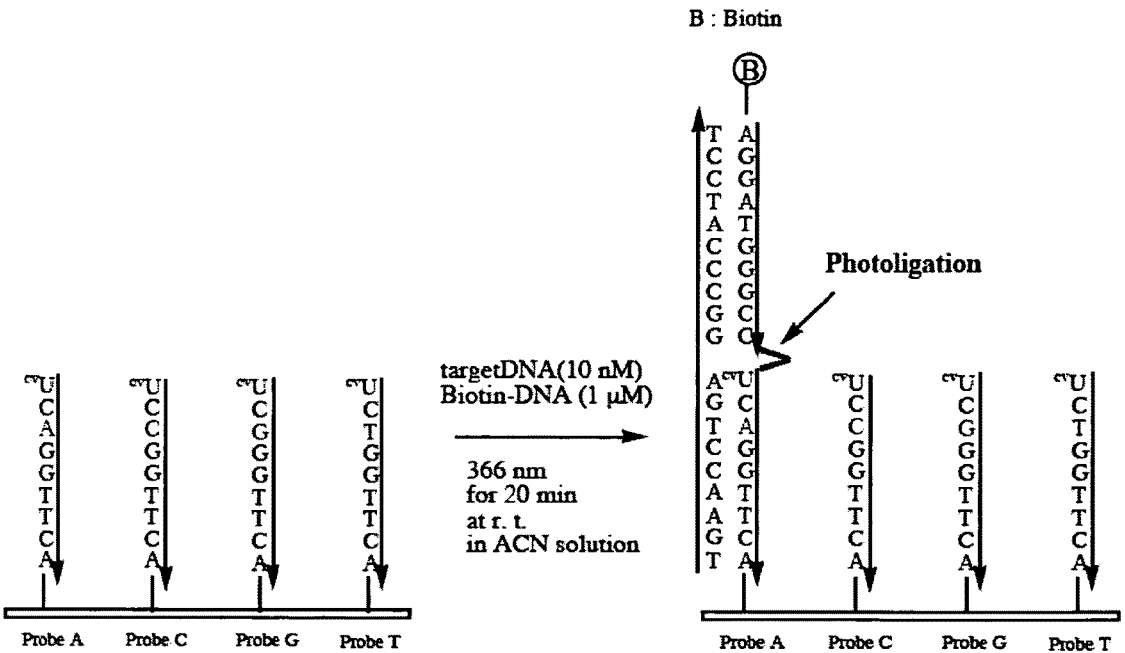
FIG. 9 is an explanatory diagram showing an embodiment of the detection of SNPs according to the present invention.

Detection of genetic polymorphism (SNPs) was carried out on a DNA chip by targeting the polymorphic part of a tumor suppressor gene p53. FIG. 9 is an explanatory diagram therefore. With regard to Probe A, Probe C, Probe G and Probe T shown on the left side, one end of each of the probes was fixed on a substrate and the other end had a photoligating base moiety ($^{CV}$U), and the 3$^{rd}$ base from the photoligating base moiety was varied to be A, C, G or T, respectively. These probes were prepared as shown in detail in FIG. 10. For each of these immobilized probes, a target DNA (10 nM) and Biotin-DNA (1 µM) were subjected to hybridization in a reaction solution containing acetonitrile at room temperature, and irradiation was performed with light having a wavelength of 366 nm for 20 minutes to conduct photoligation. Then, fluorescent avidin was allowed to bind to the biotin moiety, and detection thereof was carried out using a scanner.

Figure 11:
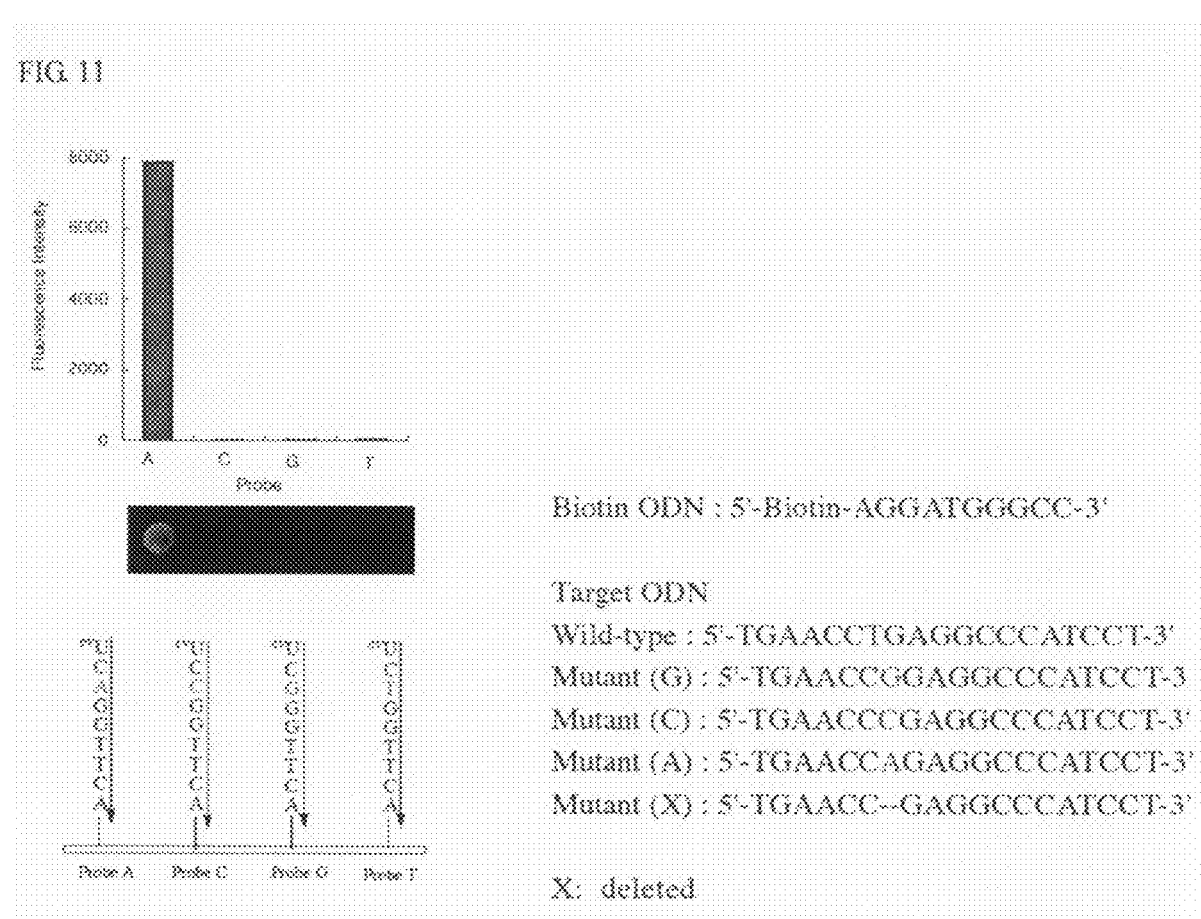
FIG. 11 shows the results of the detection of SNPs according to the present invention.

As a result, this single base substitution could be detected with a very high S/N ratio. This result is shown in FIG. 11. As can be seen from the graph of fluorescence intensity, the fluorescence intensity of Probe A showed a value 102 to 103 times the fluorescence intensity of Probe C, Probe G or Probe T.

[Examination of Effect of Adding Acetonitrile to Reaction Solvent]

Figure 12:
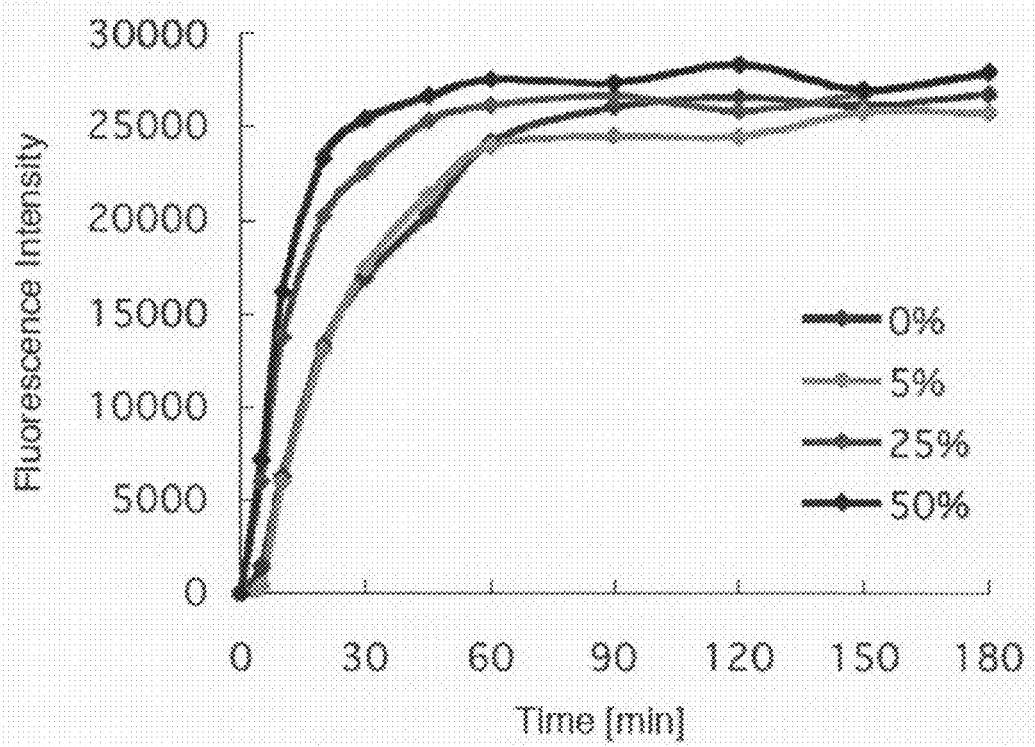
FIG. 12 shows the experimental results showing the influence of acetonitrile.
Figure 12:
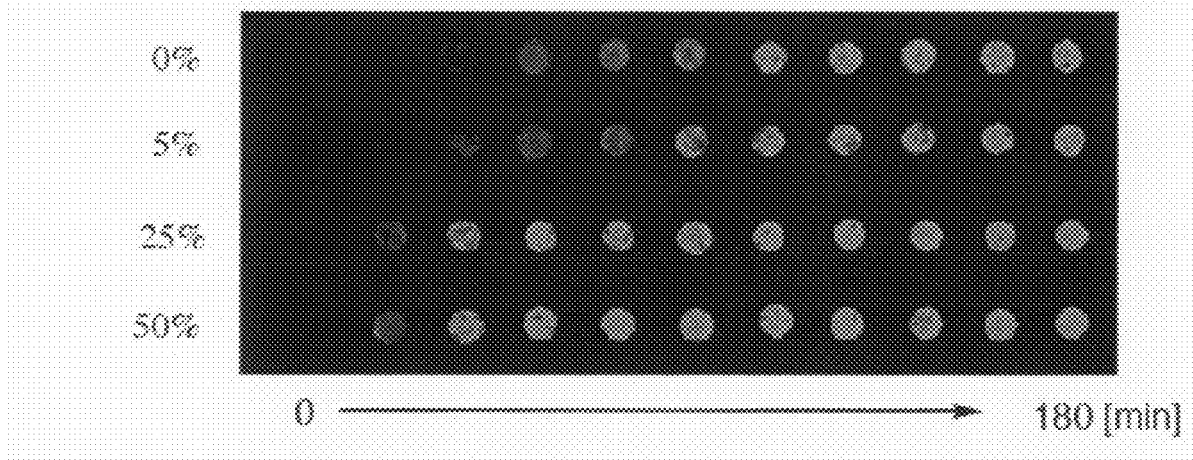

The effect of adding acetonitrile to a reaction solvent for hybridization was examined, and the results shown in FIG. 12 were obtained. As can be seen from the graph of time versus fluorescence intensity, there is an effect that an increase in the amount of addition of acetonitrile shortens the reaction time, although details of the mechanism are unclear. In other words, addition of 25% to 50% (by volume) of acetonitrile shortens the reaction time to about one-half to one-fifth, and thus detection is made possible to obtain sufficient fluorescence intensities with a duration of about 20 to 30 minutes, which is impossible with 0% to 5% of acetonitrile.

[Examination of Optimization of NaCl Concentration]

Figure 13:
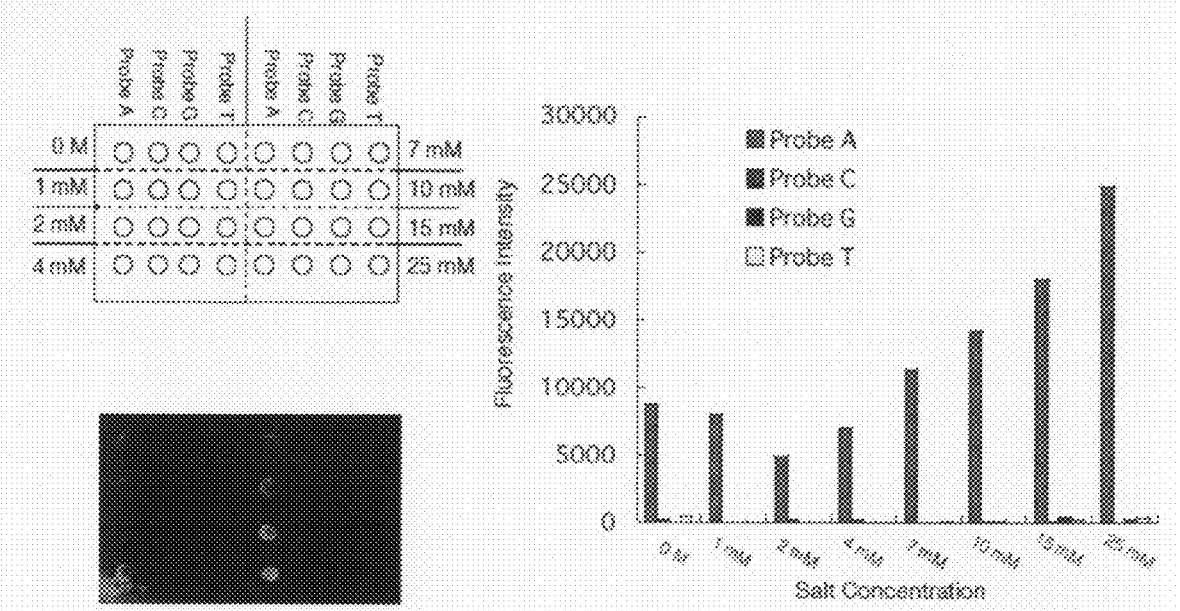
FIG. 13 shows the experimental results showing the influence of the NaCl concentration.

As shown in FIG. 13, optimization of the NaCl concentration was examined.

Figure 14:
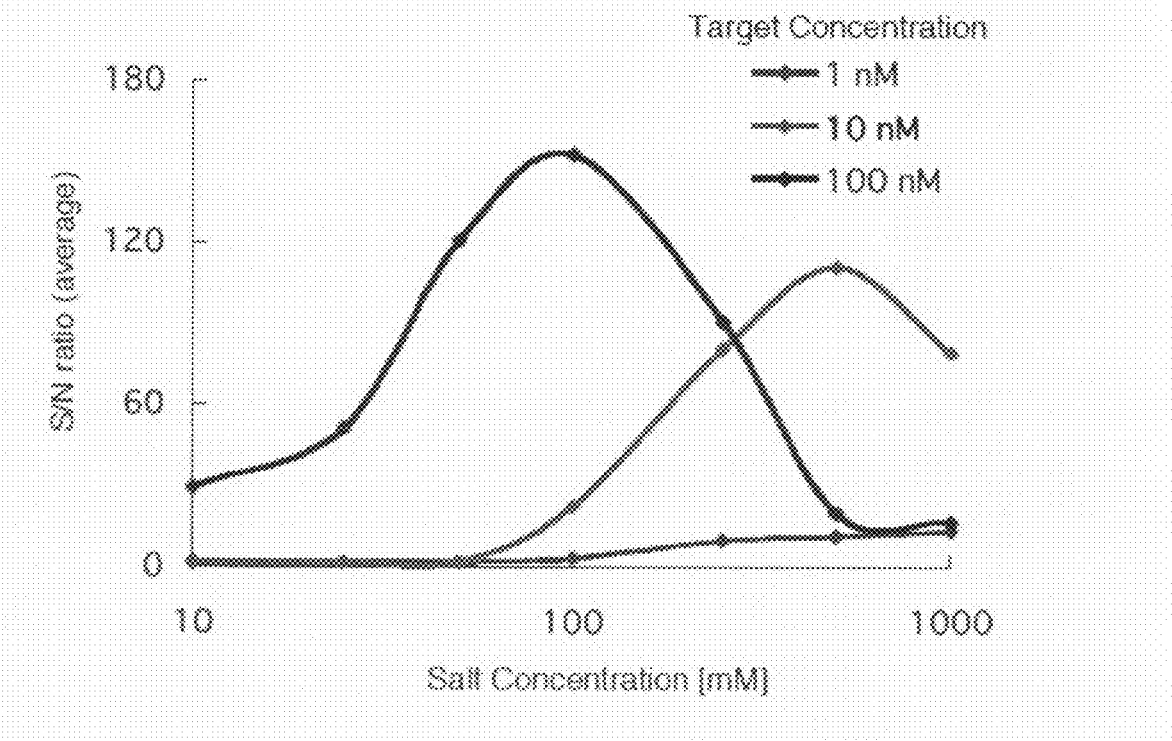
FIG. 14 shows the experimental results showing the optimum NaCl concentration for the concentration of the target nucleic acid.

The same examination was conducted over a broader range and the concentration of the target nucleic acid (ODN to be detected) was varied, so that an examination of optimization with respect to the changes combining these two conditions was carried out. These results are shown in FIG. 14. From this, it was found that there exists the optimum concentration in the salt concentration involved in hybridization, that this optimum concentration varies according to the concentration of the target nucleic acid (ODN to be detected), and that the optimum salt concentration tends to decrease as the concentration of the target nucleic acid (ODN to be detected) increases. In FIG. 14, at a concentration of the target nucleic acid (ODN to be detected) of 100 nM, the optimum salt concentration (maximum value) resides in the range of from 80 to 150 mM, centered around 100 mM. At a concentration of the target nucleic acid (ODN to be detected) of 10 nM, the optimum salt concentration (maximum value) resides in the range of from 400 to 700 mM, centered around 500 mM.

[Examination of Optimization of $MgCl_2$ Concentration]

Figure 15:
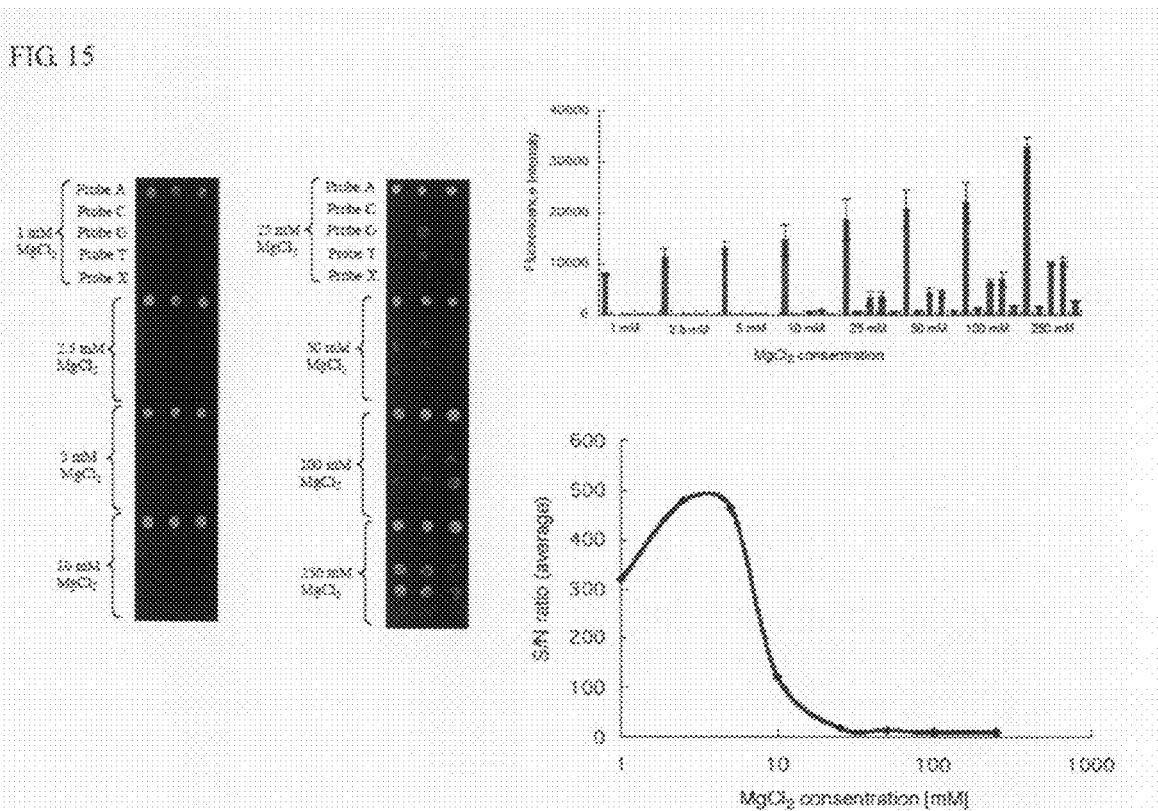
FIG. 15 shows the experimental results showing the influence of the $MgCl_2$ concentration.

Optimization of the $MgCl_2$ concentration was also examined. This result is shown in FIG. 15. The graph shows the experimental results at a concentration of the target ODN of 100 nM. In this case, the optimum concentration (maximum value) lies between 2 and 6 mM. Furthermore, optimization on the changes of the target nucleic acid (ODN to be detected) concentration was also carried out at this $MgCl_2$ concentration.

[Identification of Polymorphism by Optimal Conditions]

Figure 16:
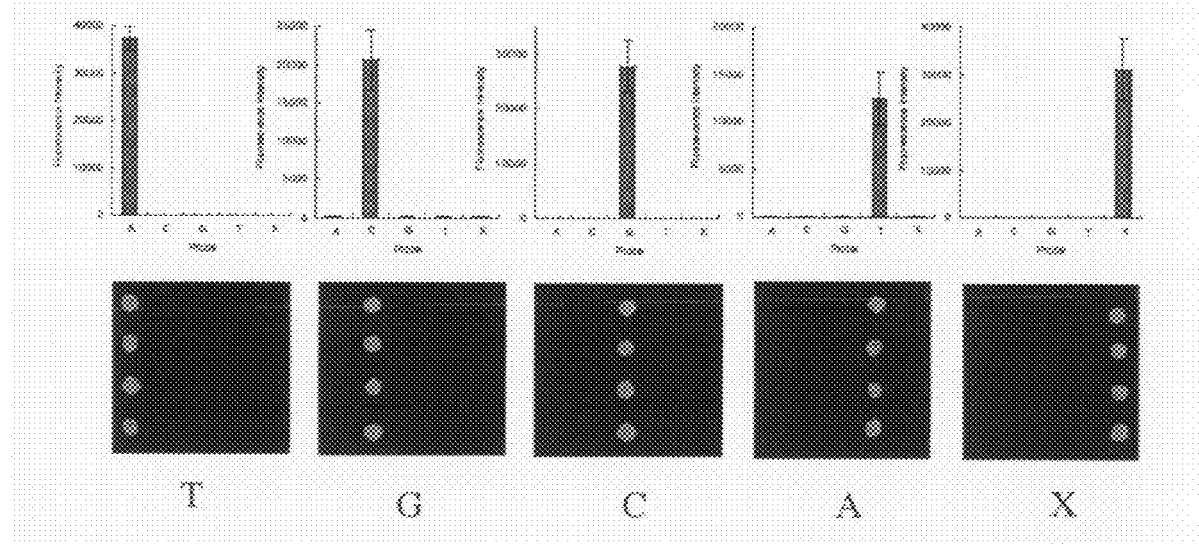
FIG. 16 shows the detection results with regard to various single nucleotide polymorphisms according to the present invention.

An experiment for identifying single base polymorphism and deletion of bases in all of the probes (4 species) was performed using the optimum conditions. An experiment was performed in the following combination of using the above-mentioned Probe A, Probe C, Probe G, Probe T and Probe X (a probe having a single base moiety deleted), and also using a complementary base sequence having polymorphism corresponding to the above-mentioned target ODN. The conditions of the target ODN (100 nM), NaCl (100 mM) and $MgCl_2$ (5 mM) were used. This result is shown in FIG. 16. As can be seen from FIG. 16, polymorphism could be identified very clearly for the polymorphism resulting from single base substitution and deletion in all of the types. This result was summarized again in terms of the S/N ratio in FIG. 17. It was found that for any type of polymorphism, polymorphism can be clearly recognized with an S/N ratio greater than $10^2$.

Example 3

The following experiment was performed in order to confirm that reversible photoligation of DNA can be achieved by using the bases used in the present invention.

Figure 18:
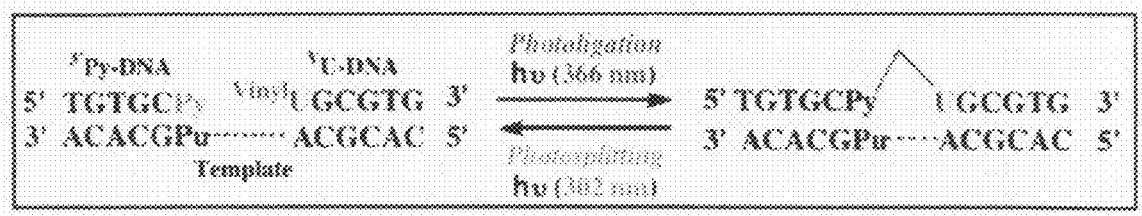
FIG. 18 is an explanatory diagram showing reversible photoligation using an uracil derivative.
Figure 18:
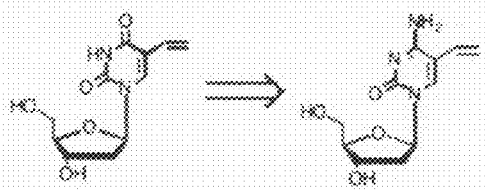

FIG. 18 is an explanatory diagram showing that reversible photoligation can be achieved by utilizing a uracil derivative as the base moiety (upper part of FIG. 18). As shown on the left side of the upper part of FIG. 18, in the presence of a 12-base long DNA strand (Template) which serves as the template, a 6-base long DNA strand having a pyrimidine base at the 3'-end ($^{3'}$Py-DNA) and a 6-base long DNA strand having a uracil derivative ($^{Vinyl}$U) at the 5'-end ($^V$U-DNA) are irradiated with light at 366 nm to photoligate the strands (reaction of the arrow directed to the right side), and thus, as shown on the left side of the upper part of FIG. 18, a 12-base long DNA strand in which Py of $^{3'}$Py-DNA and $^V$U of $^V$U-DNA are bound is produced. This 12-base long DNA strand shown on the right side of the upper part of FIG. 18 is subjected to photocleavage by photoirradiating the DNA strand with light at 302 nm (reaction of the arrow directed to the left side), and then 6-base long DNA strands shown on the left side of the upper part of FIG. 18 are generated again. Such reversible photoligation can be suitably achieved in the case of having the base of the formula shown on the left side of the lower part of FIG. 18 (uracil derivative), however, it was confirmed by the following experiment that it can also be achieved in the case of using the base of the formula shown on the right side of the lower part of FIG. 18 (cytosine derivative).

The cytosine derivative used in this experiment as the base moiety can be synthesized according to the a known method, but in the following experiment, a DNA having a cytosine derivative as the base moiety was synthesized according to the route shown in FIG. 19.

Figure 20:
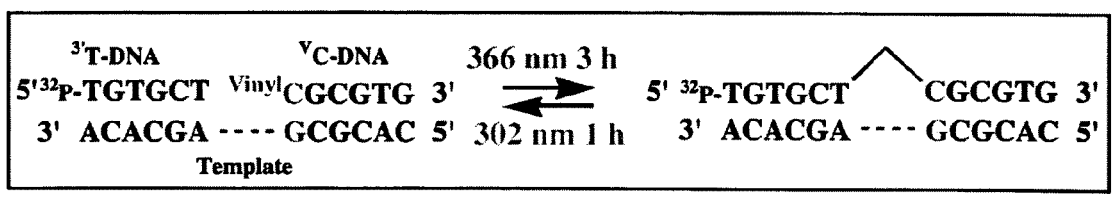
FIG. 20 shows the experimental results showing that reversible photoligation can be achieved using a cytosine derivative.
Figure 20:
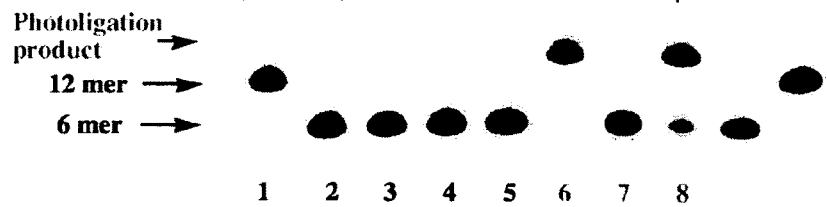

As shown in FIG. 20, reversible photoligation can be achieved using the cytosine derivative obtained as such.

As shown on the left side of the arrow of the upper part of FIG. 20, in the presence of a 12-base long DNA strand (Template) which serves as the template, a 6-base long DNA strand having a cytosine derivative($^{Vinyl}$C) at the 5'-end ($^V$C-DNA) and a 6-base long DNA strand having a radioisotope $^{32}$P at the 5'-end and thymine (T) at the 3'-end ($^{3'}$T-DNA) were irradiated with light at 366 nm (UV irradiation) for 3 hours to photoligate the strands (reaction of the arrow directed to the right side), and thus, as shown on the left side of the upper part of FIG. 20, a 12-base long DNA strand in which T of $^{3'}$T-DNA and $^V$C of $^V$C-DNA were bound was produced. This 12-base long DNA strand shown on the right side of the upper part of FIG. 20 was subjected to photocleavage by photoirradiating (UV irradiation) the DNA strand with light at 302 nm for 1 hour (reaction of the arrow directed to the left side), and then 6-base long DNA strands shown on the left side of the upper part of FIG. 20 were generated again.

In order to clarify that such results were generated by the condition of the presence of $^{3'}$T-DNA, $^V$C-DNA and Template, and the condition of the presence of the UV irradiation operation with light at 366 nm, 302 nm and 366 nm, the products obtained by altering the combinations of presence and absence of the respective conditions (+: presence and −: absence) were divided in various lanes and subjected to electrophoresis to perform autoradiography. The middle part of FIG. 20 shows these combinations, and the lower part of FIG. 20 shows the autoradiogram thus obtained. Lanes 1 and 2 are the lanes where a 12-base long DNA and a 6-base long DNA for comparison were respectively passed. Lanes numbered 3 to 8 in the lower part of FIG. 20 correspond to the respective combinations assigned with numbers 3 to 8 shown in the middle part of FIG. 20. It is shown from the comparison of Lane 6 with Lanes 3 to 5 that in order for the photoligation product (12-base long DNA strand: 12-mer) to be generated, the four factors of $^{3'}$T-DNA, $^V$C-DNA, template and photoirradiation with light at 366 nm are required. It is also shown from the comparison of Lane 6 and Lane 7 that the photoligation product once produced (12-base long DNA strand: 12-mer) again undergoes photocleavage into 6-base long DNA strands (6-mer) through photoirradiation with light at 302 nm. Furthermore, it is shown that when the 6-base long DNA strands (6-mer) thus generated through photocleavage is photoirradiated with light at 366 nm, a 12-base long DNA strand (12-mer) is produced again.

That is, it is shown that reversible photoligation can be achieved using a cytosine derivative as the base moiety.

Example 4

In order to confirm that reversible photoligation of DNA can be achieved by the bases used in the present invention, the following experiment was further performed.

In the case of using a pyrimidine base derivative (i.e., uracil derivative, thymine derivative and cytosine derivative) as the base moiety used in the present invention, a photoligating base moiety could be obtained without modifying the heterocyclic structure. In order to realize more freely reversible photoligation, it was required to obtain a photoligating base moiety using a purine base derivative, but this was very difficult. As a result of original trials and errors, the inventors of the present invention succeeded in obtaining a purine base derivative (i.e., guanine derivative and adenine derivative) which can be used as the base moiety in the present invention, by modifying the heterocyclic structure of the purine base. This modification of the heterocyclic structure of purine base is characterized by involving a 7-deaza moiety.

Figure 21:
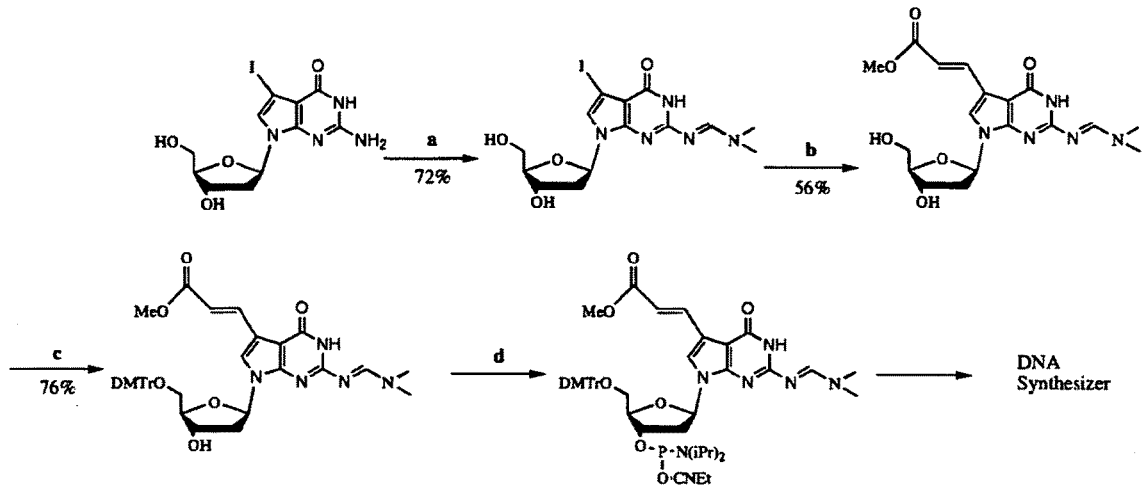
FIG. 21 is an explanatory diagram illustrating the synthesis route for a DNA having a guanine derivative as the base moiety.
Figure 22:
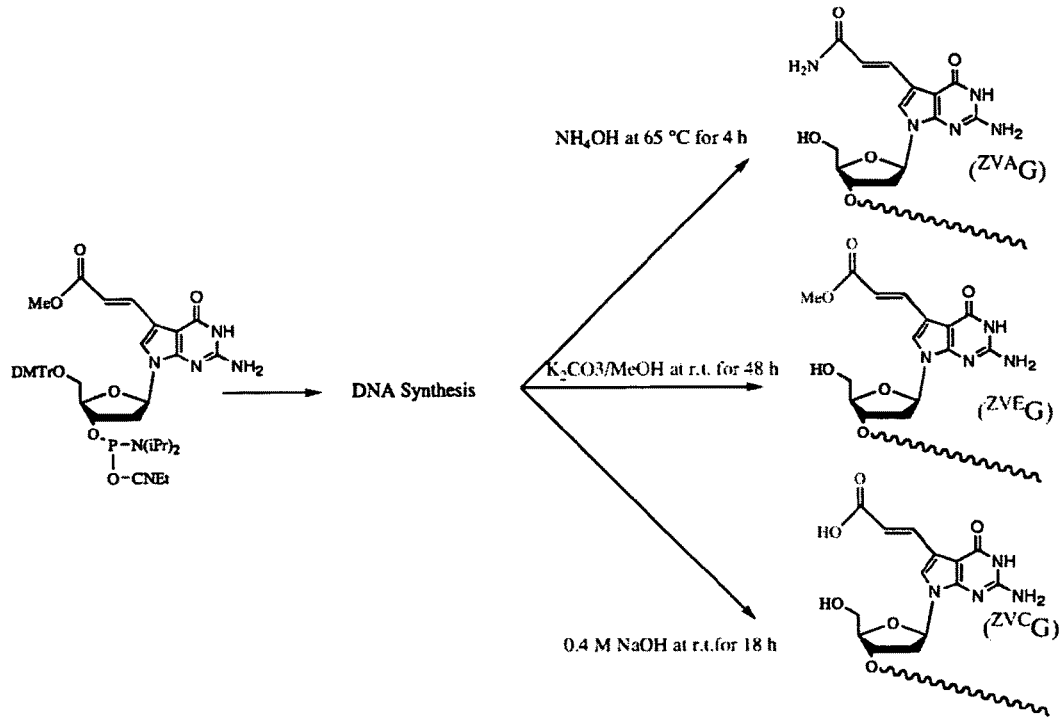
FIG. 22 is an explanatory diagram illustrating the synthesis route for a DNA having a guanine derivative as the base moiety.

FIG. 21 and FIG. 22 illustrate the structure of a guanine derivative which can be used as the base moiety in the present invention, and the synthesis route for a DNA having a guanine derivative as the base moiety. The present invention is not intended to be limited to these examples. The DNA having a guanine derivative which can be used as the base moiety according to the present invention can also be produced according to a known method.

Figure 23:
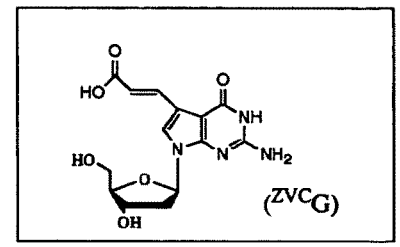
FIG. 23 shows the experimental results showing that photoligation can be achieved using a guanine derivative.
Figure 23:
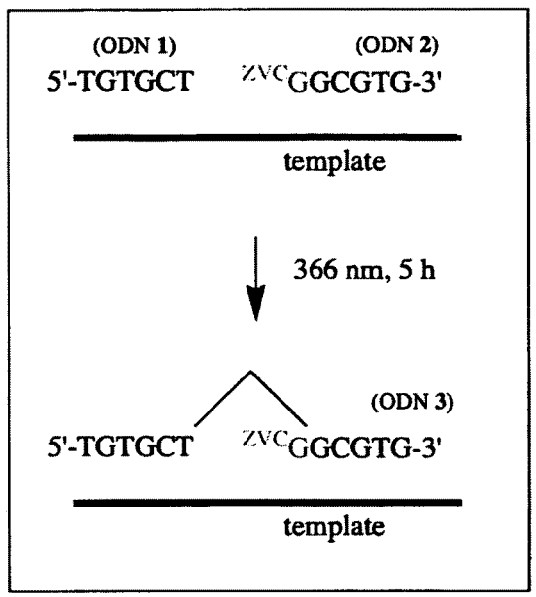
Figure 23:
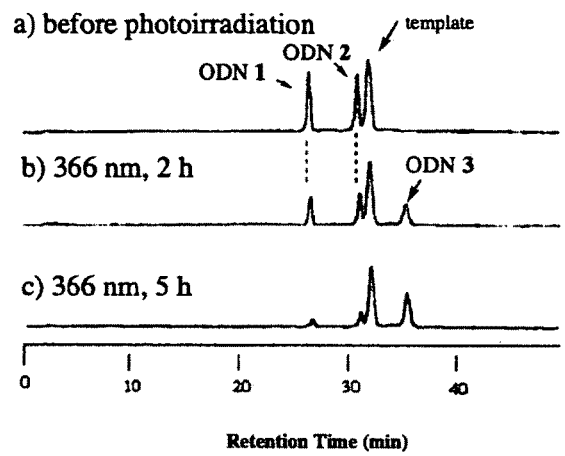

FIG. 23 shows, by means of the results of chromatography, that a 6-base long DNA strand having a guanine derivative obtained as such at the 5'-end ($^{ZVC}$G-DNA: ODN2) and a 6-base long DNA strand having T at the 3'-end (ODN1) are photoligated by photoirradiating the strands with light at 366 nm for 2 hours, and preferably for 5 hours, in the presence of a template, to produce a 12-base long DNA strand (ODN3).

Figure 24:
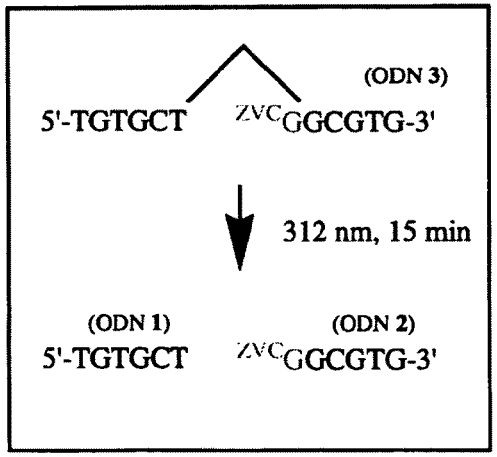
FIG. 24 shows the experimental results showing that a product of photoligation obtained using a guanine derivative can undergo photocleavage.
Figure 24:
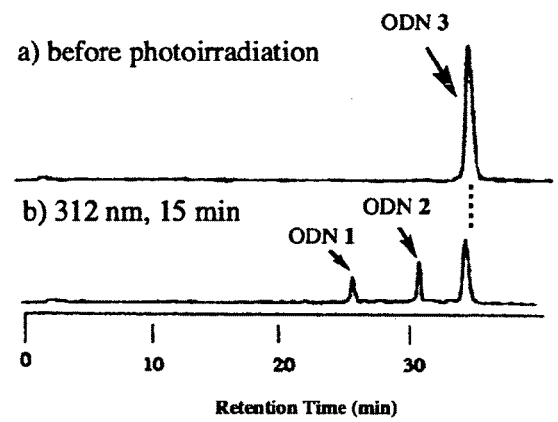

FIG. 24 shows that the 12-base long DNA strand (ODN3) obtained as shown in FIG. 23 is subjected to photocleavage by irradiating the strand with light at 312 nm for 15 minutes, to produce 6-base long DNA strands (ODN1 and ODN2) again.

That is, it is shown that reversible photoligation can be achieved using a guanine derivative as the base moiety.

Example 5

In order to confirm that reversible photoligation of DNA can be achieved by using the bases used in the present invention, the following experiment was further performed.

As a result of original trials and errors, the inventors of the present invention succeeded in obtaining a purine base derivative (i.e., guanine derivative and adenine derivative) which can be used as the base moiety in the present invention, by modifying the heterocyclic structure of the purine base. This modification of the heterocyclic structure of purine base is characterized by involving a 7-deaza moiety.

Figure 25:
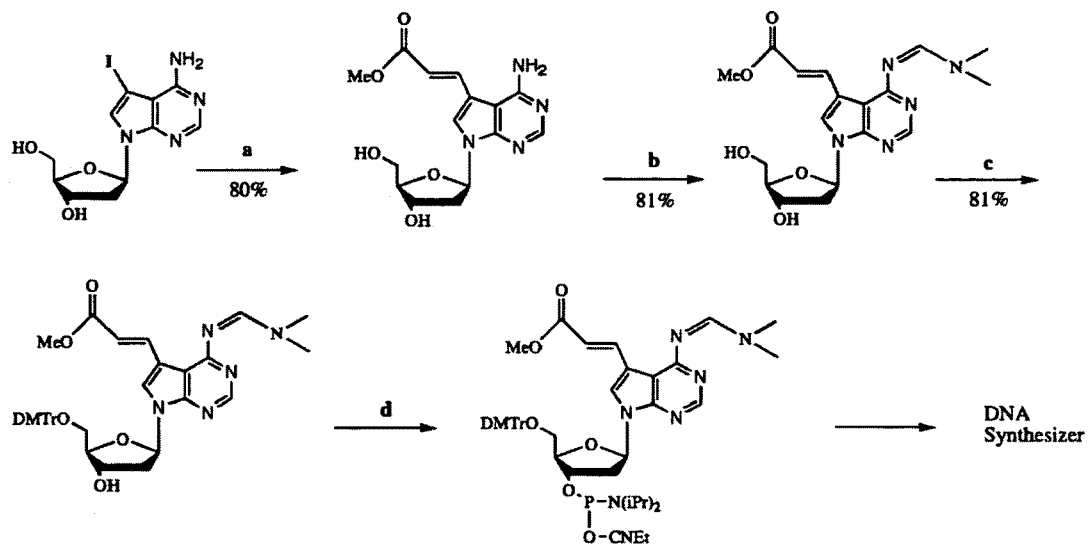
FIG. 25 is an explanatory diagram illustrating the synthesis route for a DNA having an adenine derivative as the base moiety.
Figure 26:
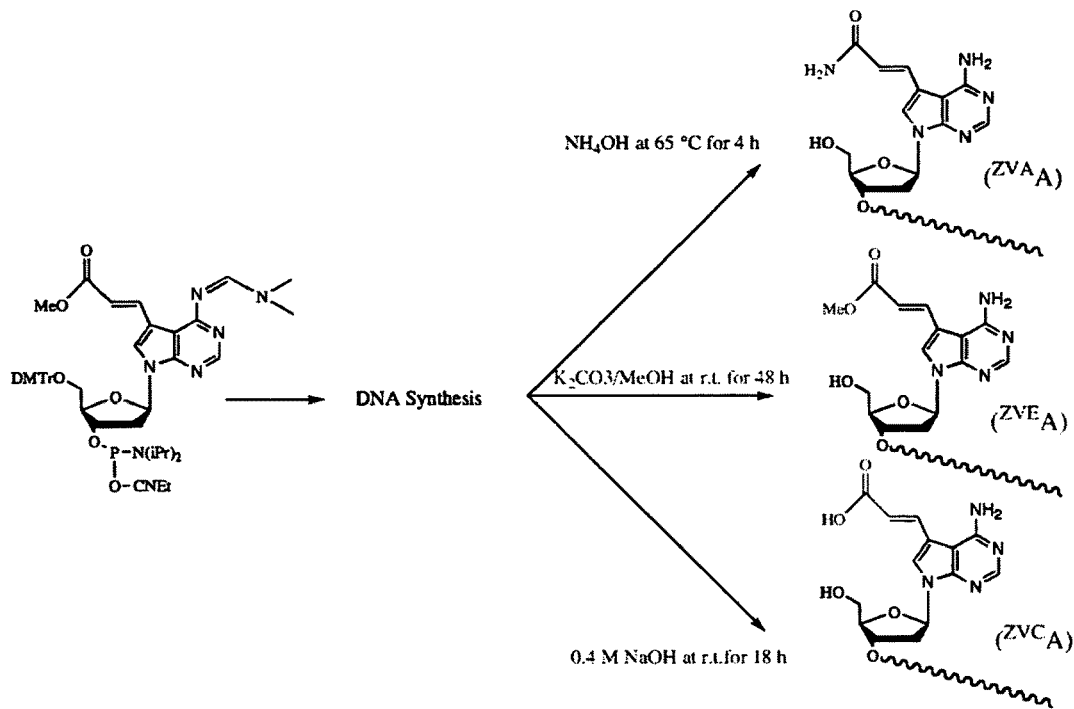
FIG. 26 is an explanatory diagram illustrating the synthesis route for a DNA having an adenine derivative as the base moiety.

FIG. 25 and FIG. 26 illustrate the structure of an adenine derivative which can be used as the base moiety in the present invention, and the synthesis route for a DNA having an adenine derivative as the base moiety. The present invention is not intended to be limited to these examples. The DNA having an adenine derivative which can be used as the base moiety according to the present invention can also be produced according to a known method.

Figure 27:
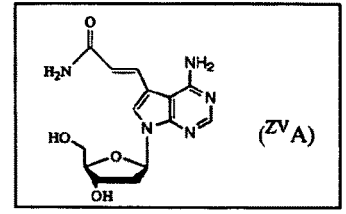
FIG. 27 shows the experimental results showing that photoligation can be achieved using an adenine derivative.
Figure 27:
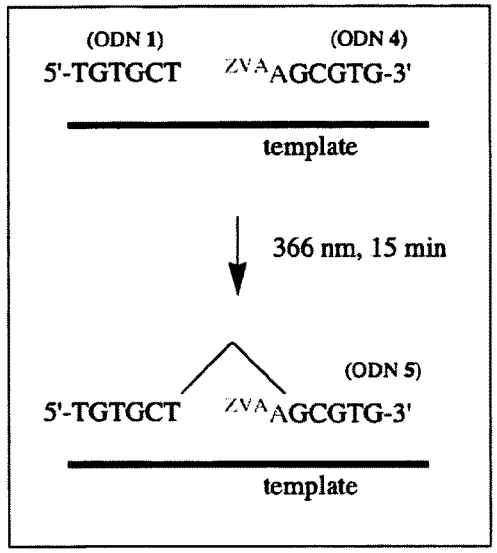
Figure 27:
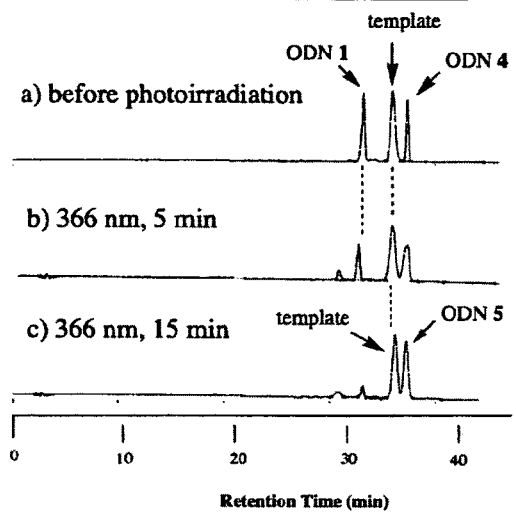

FIG. 27 shows, by means of the results of chromatography, that a 6-base long DNA strand having an adenine derivative obtained as such at the 5'-end ($^{ZVA}$A-DNA: ODN4) and a 6-base long DNA strand having T at the 3'-end (ODN1) are photoligated by photoirradiating the strands with light at 366 nm for 5 minutes, and preferably for 15 minutes, in the presence of a template, to produce a 12-base long DNA strand (ODN5).

Figure 28:
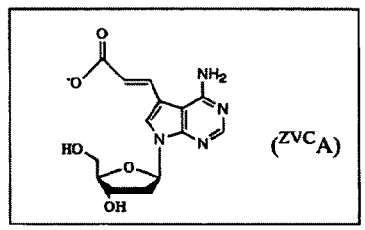
FIG. 28 shows the experimental results showing that photoligation can be achieved using an adenine derivative.
Figure 28:
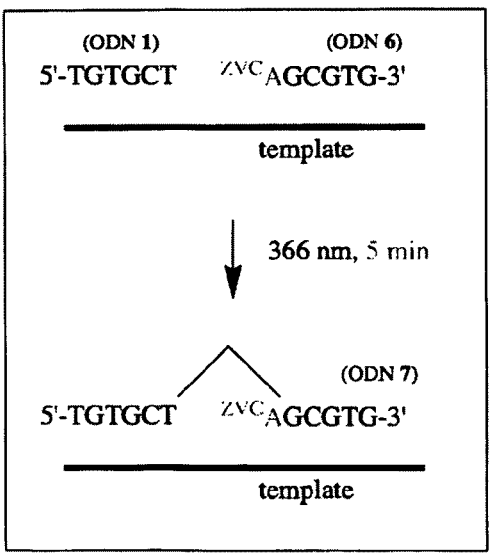
Figure 28:
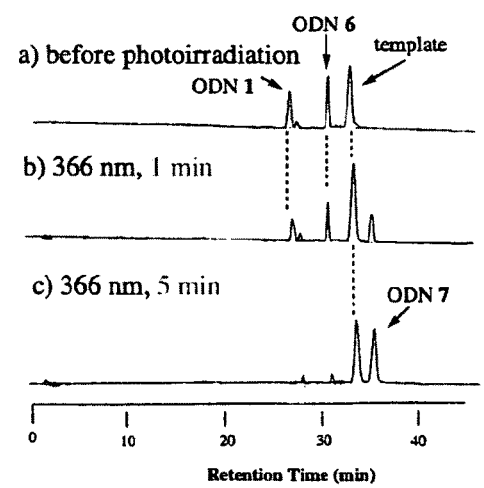

FIG. 28 shows, by means of the results of chromatography, that a 6-base long DNA strand having an adenine derivative obtained as such at the 5'-end ($^{ZVC}$A-DNA: ODN6) and a 6-base long DNA strand having T at the 3'-end (ODN1) are photoligated by photoirradiating the strands with light at 366 nm for 1 minute, and preferably for 5 minutes, in the presence of a template, to produce a 12-base long DNA strand (ODN7).

Figure 29:
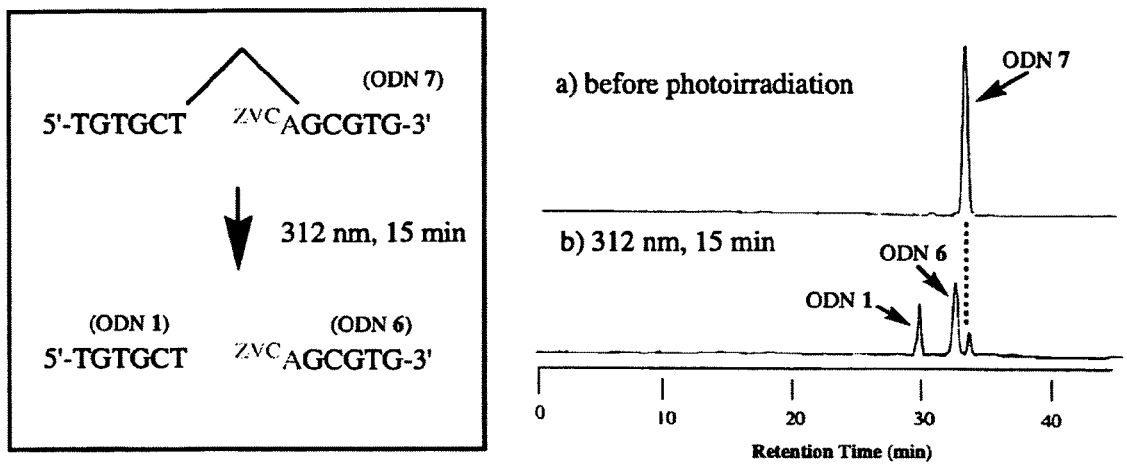
FIG. 29 shows the experimental results showing that a product of photoligation obtained using an adenine derivative can undergo photocleavage.

FIG. 29 shows that the 12-base long DNA strand (ODN7) obtained as shown in FIG. 28 is subjected to photocleavage by irradiating the strand with light at 312 nm for 15 minutes, to produce 6-base long DNA strands (ODN1 and ODN6) again.

That is, it is shown that reversible photoligation can be achieved using an adenine derivative as the base moiety.

Figure 30:
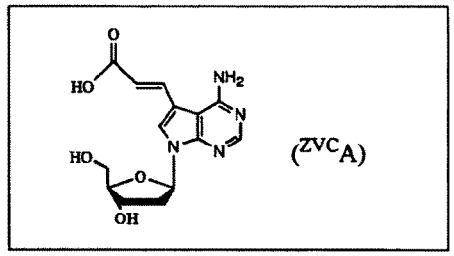
FIG. 30 shows the experimental results showing the UV absorption properties of 7-carboxyvinyl-7-deaza-2'-deoxyadenosine.
Figure 30:
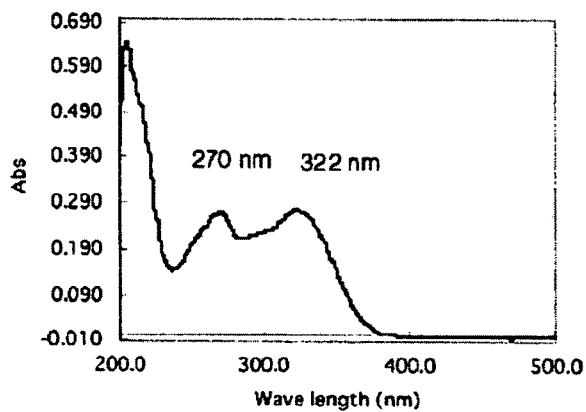

FIG. 30 shows the UV absorption properties of 7-carboxyvinyl-7-deaza-2'-deoxyadenosine, which is a deoxynucleoside having a particularly suitable adenine derivative as the base moiety ($^{ZVC}$A).

FIG. 1 shows a strategy for detection of an RNA point mutation on a DNA chip.

Figure 2:
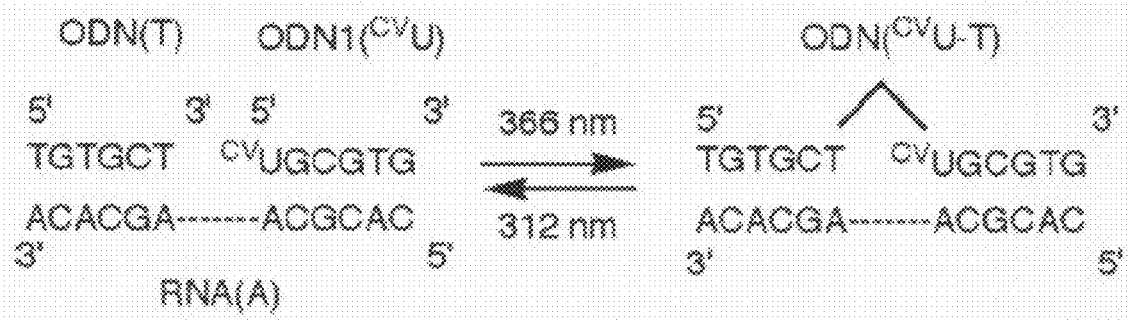
FIG. 2 is an explanatory diagram illustrating the photoligation of nucleic acids using an RNA as the template.
Figure 3:
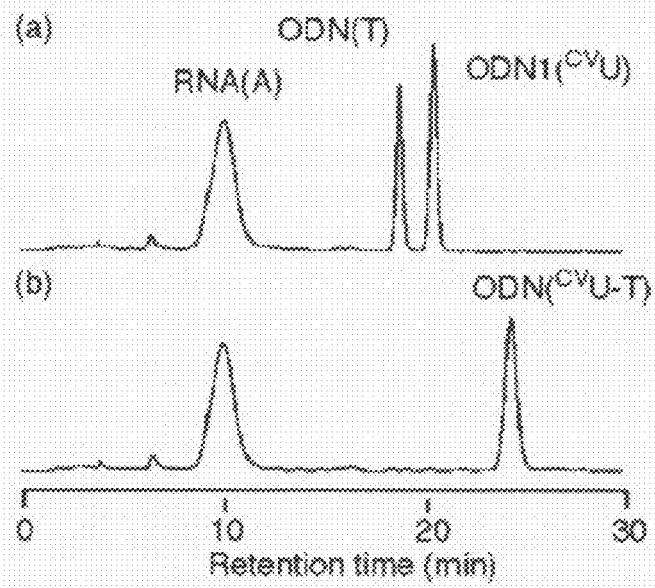
FIG. 3 is an HPLC chart showing the photoligation of nucleic acids using an RNA as the template.

FIG. 2 shows RNA template-directed reversible photoligation of ODN by means of $^{CV}$U.

FIG. 3 shows the HPLC analysis results for ODN1($^{CV}$U) and ODN(T) irradiated in the presence of a template RNA(A). (a) is before irradiation, and (b) is irradiation for 30 minutes at 366 nm, yield 98%.

FIG. 4 shows the fluorescence intensities (upper) and an image (lower) obtained with a microarray scanner of photoligation products based on matched and single-mismatched target RNA.

FIG. 5 shows the HPLC analysis results for irradiated ODN($^{CV}$U-T). (a) is before irradiation, and (b) is irradiation for 4 minutes at 312 nm.

FIG. 6 shows the HPLC analysis results for irradiated ODN1($^{CV}$U). (a) is before irradiation, and (b) is irradiation for 2 minutes at 312 nm.

FIG. 7 shows the fluorescent intensities (upper) and an image (lower) of photoligatino products of ODN2($^{CV}$U.

FIG. 8 shows photoligation on a DNA chip.

FIG. 9 shows detection of genetic polymorphism (SNPs) on a DNA chip.

Figure 10:
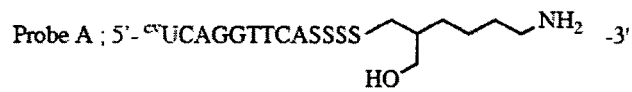
FIG. 10 is an explanatory diagram showing an exemplary preparation of a photoligating nucleic acid of the present invention.
Figure 10:
Figure 10:
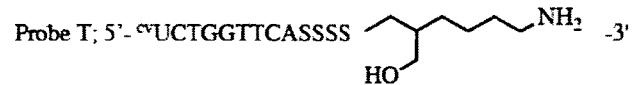
Figure 10:
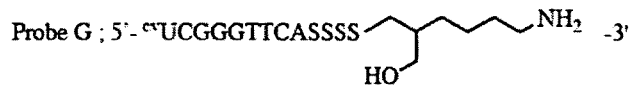

FIG. 10 shows preparation of probe ODNs.

FIG. 11 shows detection of a single base substitution at a high S/N ratio.

FIG. 12 shows the effects of adding acetonitrile to the reaction solvent.

FIG. 13 shows optimization of the NaCl concentration.

FIG. 14 shows optimization of combining the two conditions, namely, the concentration of the target nucleic acid (ODN to be detected) and the concentration of salt.

FIG. 15 shows optimization of the $MgCl_2$ concentration.

FIG. 16 shows distinction based on single base polymorphism and deletion of the four species of base.

Figure 17:
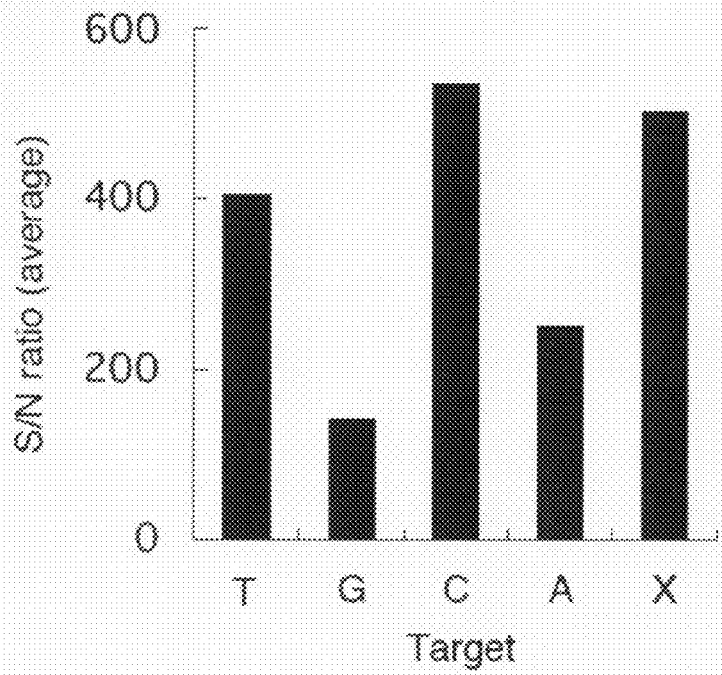
FIG. 17 shows the S/N ratio from the detection of various single nucleotide polymorphisms according to the present invention.

FIG. 17 shows the S/N ratios in the distinction based on single base polymorphism and deletion of the four species of base.

FIG. 18 is an explanatory diagram showing reversible photoligation utilizing a uracil derivative.

Figure 19:
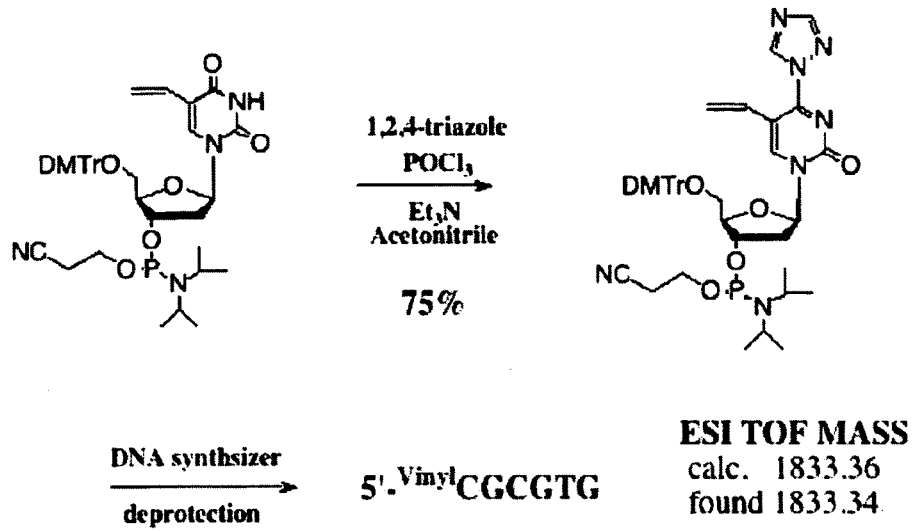
FIG. 19 is an explanatory diagram illustrating the synthesis route for a DNA having a cytosine derivative as the base moiety.

FIG. 19 is an explanatory diagram illustrating the synthesis route for a DNA having a cytosine derivative as the base moiety.

FIG. 20 shows the experimental results indicating that reversible photoligation can be achieved using a cytosine derivative.

FIG. 21 is an explanatory diagram illustrating the synthesis route for a DNA having a guanine derivative as the base moiety.

FIG. 22 is an explanatory diagram illustrating the synthesis route for a DNA having a guanine derivative as the base moiety.

FIG. 23 shows the experimental results indicating that photoligation can be achieved using a guanine derivative.

FIG. 24 shows the experimental results indicating that a product of photoligation obtained using a guanine derivative can undergo photocleavage.

FIG. 25 is an explanatory diagram illustrating the synthesis route for a DNA having an adenine derivative as the base moiety.

FIG. 26 is an explanatory diagram illustrating the synthesis route for a DNA having an adenine derivative as the base moiety.

FIG. 27 shows the experimental results indicating that photoligation can be achieved using an adenine derivative.

FIG. 28 shows the experimental results indicating that photoligation can be achieved using an adenine derivative.

FIG. 29 shows the experimental results indicating that a product of photoligation obtained using an adenine derivative can undergo photocleavage.

FIG. 30 shows the experimental results showing the UV absorption properties of 7-carboxyvinyl-7-deaza-2'-deoxy-adenosine.

Table 1 shows the fluorescence intensities normalized to that of the photoligation product of ODN2($^{CV}$U), of products which properly formed base pairs with eight RNA targets differing from each other at a single nucleotide position. [a]: The underlined characters represent mismatch bases. [b]: The experiments were each performed at least four times.

TABLE 1

Comparison of fluorescence intensities of point-mutated target RNAs (SEQ ID NOS 1 and 3-9, respectively, in order of appearance)

| Target RNA[a] | | Fluorescence Intensity[b] |
|---|---|---|
| RNA(A) | 5'-r(CACGCAAGCACA)-3' | 1.0 ± 0.02 |
| RNA(7U) | 5'-r(CACGCAUGCACA)-3' | 0.04 ± 0.009 |
| RNA(8U) | 5'-r(CACGCAAUCACA)-3' | 0.07 ± 0.03 |
| RNA(9U) | 5'-r(CACGCAAGUACA)-3' | 0.03 ± 0.01 |
| RNA(10U) | 5'-r(CACGCAAGCUCA)-3' | 0.05 ± 0.007 |
| RNA(11U) | 5'-r(CACGCAAGCAUA)-3' | 0.10 ± 0.03 |
| RNA(9A) | 5'-r(CACGCAAGAACA)-3' | 0.03 ± 0.02 |
| RNA(9G) | 5'-r(CACGCAAGGACA)-3' | 0.09 ± 0.005 |

Table 2 shows the fluorescence intensities normalized to that of the photoligation product of ODN2($^{CV}$U). [a]: The underlined characters represent mismatch bases. [b]: The experiments were each performed at least four times.

TABLE 2

Comparison of fluorescence intensities of point-mutated target RNAs (SEQ ID NOS 1 and 10-12, respectively, in order of appearance)

| Target RNA[a] | | Intensity[b] |
|---|---|---|
| RNA(A) | 5'-r(CACGCAAGCACA)-3' | 1.0 ± 0.15 |
| RNA(6G) | 5'-r(CACGCGAGCACA)-3' | 0.08 ± 0.009 |
| RNA(6C) | 5'-r(CACGCCAGCACA)-3' | 0.04 ± 0.01 |
| RNA(6U) | 5'-r(CACGCUAGCACA)-3' | 0.04 ± 0.02 |

The invention claimed is:

1. A method for detecting a target nucleic acid having a specific base sequence contained in a nucleic acid mixture, wherein:

utilizing a set of nucleic acids for detecting a target nucleic acid having a specific base sequence, which the set of nucleic acids includes a photoligating nucleic acid comprising a nucleic acid having a group represehted by the following Formula I, Formula II, Formula III, Formula IV or Formula V:

[Formula I]

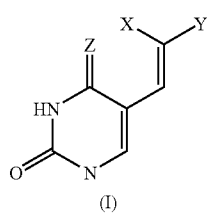

[Chemical Formula 12]

wherein Z represents O or NH; at least one of X and Y represents an electron-withdrawing group selected from the group consisting of a carboxyl group, a lower alkoxycarbonyl group, a substituted amide group and a cyano group; and the remainder of X and Y represents a hydrogen atom;

[Formula II]

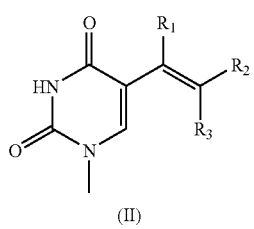

[Chemical Formula 13]

wherein $R_1$ is a hydrogen atom; at least one of $R_2$ and $R_3$ represents a group selected from the group consisting of a carboxyl group, a lower alkoxycarbonyl group, a lower alkenyl group, a lower alkynyl group, a substituted amide group, an amide group, a cyano group and a hydrogen atom; and the remainder of $R_2$ and $R_3$ represents a hydrogen atom or a cyano group;

[Formula III]

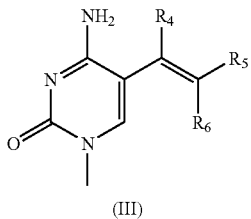

[Chemical Formula 14]

wherein $R_4$ is a hydrogen atom or a lower alkyl group; at least one of $R_5$ and $R_6$ represents a group selected from the group consisting of a carboxyl group, a lower alkoxycarbonyl group, a lower alkenyl group, a lower alkynyl group, a substituted amide group, an amide group, a cyano group and a hydrogen atom; and the remainder of $R_5$ and $R_6$ represents a hydrogen atom or a cyano group;

[Formula IV]

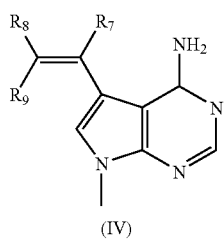

[Chemical Formula 15]

wherein $R_7$ is a hydrogen atom or a lower alkyl group; at least one of $R_8$ and $R_9$ represents a group selected from the group consisting of a carboxyl group, a lower alkoxycarbonyl group, a lower alkenyl group, a lower alkynyl group, a substituted amide group, an amide group, a cyano group and a hydrogen atom; and the remainder of $R_8$ and $R_9$ represents a hydrogen atom or a cyano group;

[Formula V]

[Chemical Formula 16]

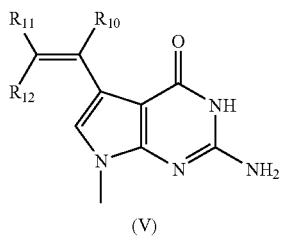

(V)

wherein $R_{10}$ is a hydrogen atom or a lower alkyl group; at least one of $R_{11}$ and $R_{12}$ represents a group selected from the group consisting of a carboxyl group, a lower alkoxycarbonyl group, a lower alkenyl group, a lower alkynyl group, a substituted amide group, an amide group, a cyano group and a hydrogen atom; and the remainder of $R_{11}$ and $R_{12}$ represents a hydrogen atom or a cyano group;

at the 5'-end or 3'-end as a base moiety, and a nucleic acid to be photoligated having a base having a carbon-carbon double bond at the 3'-end or 5'-end as a base moiety capable of being photoligated to the photoligating nucleic acid, wherein any one of the photoligating nucleic acid and the nucleic acid to be photoligated has a labeling moiety, while the other one not having a labeling moiety between the photoligating nucleic acid and the nucleic acid to be photoligated is immobilized on a substrate in advance;

a nucleic acid having a base sequence that is complementary to the base sequence of the target nucleic acid having a specific base sequence, can be generated by photoligation of the photoligating nucleic acid and the nucleic acid to be photoligated; and the nucleic acid that can be generated by photoligation of the photoligating nucleic acid and the nucleic acid to be photoligated, can be washed under a washing condition capable of dissociating complementary double strands, wherein the method comprises the following steps of:

hybridizing the target nucleic acid having a specific base sequence contained in a nucleic acid mixture with the photoligating nucleic acid and the nucleic acid to be photoligated;

immobilizing a nucleic acid having a labeling moiety on a substrate by photoirradiating the nucleic acid to result in photoligation of the nucleic acid with the photoligating nucleic acid and nucleic acid to be photoliqated that have been brought adjacent in a manner capable of photoligating through the hybridization using the target nucleic acid having a specific base sequence as the template;

removing any nucleic acid having a labeling moiety and not immobilized on the substrate through photoligation by washing the nucleic acid having a labeling moiety and immobilized on the substrate through photoligation, under a washing condition capable of dissociating hybridized complementary double strands; and detecting the labeling moiety so as to detect the nucleic acid having a labeling moiety and immobilized on the substrate through photoligation;

wherein the washing condition involves washing at a washing temperature in the range of 80° C. to 100° C.;

wherein the process of hybridization and the process of immobilizing a nucleic acid having a labeling moiety through photoligation on the substrate are carried out in a reaction solution containing a salt having buffering effects;

wherein the reaction solution contains 20% to 60% v/v of a water-dispersible organic solvent; and wherein the salt having buffering effects is a cacodylic acid salt.

2. The method according to claim 1 wherein the base moiety is a group represented by Formula I, and in the Formula I, Z is O; X is a hydrogen atom; and Y is a carboxyl group, a lower alkoxycarbonyl group, a substituted amide group or a cyano group.

3. The method according to claim 1 wherein the base moiety is a group represented by Formula II, and in the Formula II, at least one of $R_2$ and $R_3$ represents a group selected from the group consisting of a carboxyl group, a lower alkoxycarbonyl group, a substituted amide group, an amide group, a cyano group and a hydrogen atom; and the remainder of $R_2$ and $R_3$ is a hydrogen atom.

4. The method according to claim 1 wherein the base moiety is a group represented by Formula III, and in the Formula III, at least one of $R_5$ and $R_6$ represents a group selected from the group consisting of a carboxyl group, a lower alkoxycarbonyl group, a substituted amide group, an amide group, a cyano group and a hydrogen atom; and the remainder of $R_5$ and $R_6$ is a hydrogen atom.

5. The method according to claim 1 wherein the base moiety is a group represented by Formula IV, and in the Formula IV, at least one of $R_8$ and $R_9$ represents a group selected from the group consisting of a carboxyl group, a lower alkoxycarbonyl group, a substituted amide group, an amide group, a cyano group and a hydrogen atom; and the remainder of $R_8$ and $R_9$ is a hydrogen atom.

6. The method according to claim 1 wherein the base moiety is a group represented by Formula V, and in the Formula V, at least one of $R_{11}$ and $R_{12}$ represents a group selected from the group consisting of a carboxyl group, a lower alkoxycarbonyl group, a substituted amide group, an amide group, a cyano group and a hydrogen atom; and the remainder of $R_{11}$ and $R_{12}$ is a hydrogen atom.

7. The method according to claim 1 which comprises any label selected from the group consisting of biotin labels, dye labels and RI labels as a labeling moiety.

8. The method according to claim 1 wherein either one of photoligating nucleic acid and the nucleic acid to be photoligated which is immobilized on a substrate in advance Is immobilized on the substrate via a linker moiety.

9. The method according to claim 8 wherein the linker moiety comprises polyethylene glycol or an alkane.

10. The method according to claim 1 wherein the substrate is any one selected from the group consisting of a glass plate, CPG, and polystyrene beads.

11. The method according to claim 1 wherein the base ,having a carbon-carbon double bond is cytosine, thymine or uracil.

12. The method according to claim 1 wherein the photoligating nucleic acid is an oligonucleotide.

13. The method according to claim 1 wherein the photoligating nucleic acid is a DNA.

14. The method according to claim 1 wherein the photoligating nucleic acid is an RNA.

15. The method according to claim 1 wherein the photoligating nucleic acid is a peptide nucleic acid.

16. The method according to claim 1 wherein the nucleic acid to be photoliaated is an oligonucleotide.

17. The method according to claim 1 wherein the nucleic acid to be photoliaated is a DNA.

18. The method according to claim 1 wherein the nucleic acid to be photoligated is an RNA.

19. The method according to claim 1 wherein the nucleic acid to be photoliaated is a peptide nucleic acid.

20. The method according to claim 1 wherein the photoligating nucleic acid and the nucleic acid to be photoliaated are nucleic acids of the same kind.

21. The method according to claim 1 wherein a DNA microarray having either one of the photoligating nucleic acid and the nucleic acid to be photoliaated, which does not have a labeling moiety and is immobilized on a substrate, is used together with the other one of the photoligating nucleic acid and the nucleic acid to be photoligated, which is not immobilized on a substrate and has a labeling moiety.

22. The method according to claim 1 wherein the process of hybridization and the process of immobilizing a nucleic acid having a labeling moiety on a substrate by photoligation are carried out at a temperature of 20° C. to 30° C.

23. The method according to claim 1 wherein the pH of the reaction solution is in the range of 6.5 to 8.5.

24. The method according to claim 1 wherein the concentration of the salt having buffering effects is in the range of 5 to 250 mM.

25. The method according to claim 1 wherein the water-dispersible organic solvent is acetonitrile.

26. The method according to claim 1 wherein the reaction solution contains a salt of an alkali metal and/or alkaline earth metal, and the concentration of the salt is optimized with respect to the concentration of the target nucleic acid.

27. The method according to claim 26 which comprises sodium chloride and/or magnesium chloride as the salt of alkali metal and/or alkaline earth metal.

28. The method according to claim 1 wherein the photoirradiating is performed by irradiating with light having a wavelength of 330 nm or longer.

29. The method according to claim 1 wherein the washing condition involves washing at a washing temperature in the range of 95° C. to 100° C.

30. The method according to claim 1 wherein the washing condition involves washing with a washing solution containing a denaturing agent.

31. The method according to claim 1 wherein the washing condition involves washing with a washing solution containing a surfactant.

32. The method according to claim 1 wherein the label of the labeling moiety is a fluorescent dye label, and the process of detecting the labeling moiety includes process of performing fluorescence measurement using a laser scanner.

33. The method according to claim 1 wherein the label of the labeling moiety is a biotin label, and the process of detecting the labeling moiety includes process of performing a biotin-avidin binding reaction using a fluorescent dye-labeled avidin and process of performing fluorescence measurement using a laser scanner.

34. The method according to claim 1 for detecting point mutation in the base sequence of the target nucleic acid by using a photoligating nucleic acid and a nucleic acid to be photoligated, wherein a nucleic acid having a sequence having a single base substitution from a base sequence that is complementary to the base sequence of the target nucleic acid having a specific base sequence comprises a base sequence that would be generated by photoligation of the photoligating nucleic acid and the nucleic acid to be photoligated.

35. A method for detecting a target nucleic acid having a specific base sequence contained in a nucleic acid mixture, comprising:

utilizing a set of nucleic acids for detecting a target nucleic acid having a specific base sequence, which the set of nucleic acids includes a photoligating nucleic acid comprising a nucleic acid having a group represented by the following Formula I, Formula II, Formula III, Formula IV or Formula V:

[Formula I]

[Chemical Formula 12]

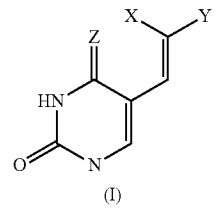

(I)

wherein Z represents O or NH; at least one of X and Y represents an electron-withdrawing group selected from the group consisting of a carboxyl group, a lower alkoxycarbonyl group, a substituted amide group and a cyano group; and the remainder of X and Y represents a hydrogen atom;

[Formula II]

[Chemical Formula 13]

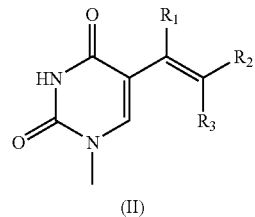

(II)

wherein $R_1$ is a hydrogen atom; at least one of $R_2$ and $R_3$ represents a group selected from the group consisting of a carboxyl group, a lower alkoxycarbonyl group, a lower alkenyl group, a lower alkynyl group, a substituted amide group, an amide group, a cyano group and a hydrogen atom; and the remainder of $R_2$ and $R_3$ represents a hydrogen atom or a cyano group;

[Formula III]

[Chemical Formula 14]

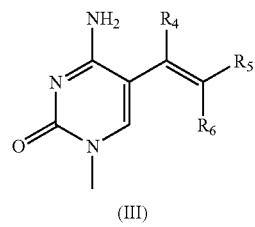

(III)

wherein $R_4$ is a hydrogen atom or a lower alkyl group; at least one of $R_5$ and $R_6$ represents a group selected from the group consisting of a carboxyl group, a lower alkoxycarbonyl group, a lower alkenyl group, a lower alkynyl group, a substituted amide group,. an amide group, a cyano group and a hydrogen atom; and the remainder of $R_5$ and $R_6$ represents a hydrogen atom or a cyano group;

[Formula IV]

[Chemical Formula 15]

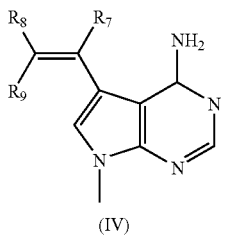

(IV)

wherein $R_7$ is a hydrogen atom or a lower alkyl group; at least one of $R_8$ and $R_9$ represents a group selected from the group consisting of a carboxyl group, a lower alkoxycarbonyl group, a lower alkenyl group, a lower alkynyl group, a substituted amide group, an amide group, a cyano group and a hydrogen atom; and the remainder of $R_8$ and $R_9$ represents a hydrogen atom or a cyano group;

[Formula V]

[Chemical Formula 16]

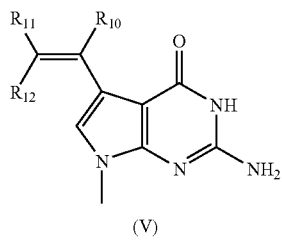

(V)

wherein $R_{10}$ is a hydrogen atom or a lower alkyl group; at least one of $R_{11}$ and $R_{12}$ represents a group selected from the group consisting of a carboxyl group, a lower alkoxycarbonyl group, a lower alkenyl group, a lower alkynyl group, a substituted amide group, an amide group, a cyano group and a hydrogen atom; and the remainder of $R_{11}$ and $R_{12}$ represents a hydrogen atom or a cyano group;
 at the 5'-end or 3'-end as a base moiety, and
 a nucleic acid to be photoligated having a base having a carbon -carbon double bond at the 3'-end or 5'-end as a base moiety capable of being photoligated to the photoligating nucleic acid,
 wherein any one of the photoligating nucleic acid and the nucleic acid to be photoligated has a labeling moiety, while the other one not having a labeling moiety between the photoligating nucleic acid and the nucleic acid to be photoligated is immobilized on a substrate in advance;
 a nucleic acid having a base sequence that is complementary to the base sequence of the target nucleic acid having a specific base sequence, can be generated by photoligation of the photoligating nucleic acid and the nucleic acid to be photoligated; and
 the nucleic acid that can be generated by photoligation of the photoligating nucleic acid and the nucleic acid to be photoligated, can be washed under a washing condition capable of dissociating complementary double strands,
 wherein the method comprises steps of:
 hybridizing the target nucleic acid having a specific base sequence contained in a nucleic acid mixture with the photoligating nucleic acid and the nucleic acid to be photoligated;
 immobilizing a nucleic acid having a labeling moiety on a substrate by photoirradiating the nucleic acid to result in photoligation of the nucleic acid with the photoligating nucleic acid and nucleic acid to be photoligated, that have been brought adjacent in a manner capable of photoligating through the hybridization using the target nucleic acid having a specific base sequence as the template;
 removing any nucleic acid having a labeling moiety and not immobilized on the substrate through photoligation by washing the nucleic acid having a labeling moiety and immobilized on the substrate through photoligation, under a washing condition capable of dissociating hybridized complementary double strands; and
 detecting the labeling moiety so as to detect the nucleic acid having a labeling moiety and immobilized on the substrate through photoligation.

36. The method of claim 35 wherein the process of hybridization and the process of immobilizing a nucleic acid having a labeling moiety through photoligation on the substrate are carried out in a reaction solution containing a salt having buffering effects; and the salt having buffering effects is a cacodylic acid salt.

37. The method of claim 1, wherein the photoligating nucleic acid comprises a nucleic acid that is a nucleic acid or a peptide nucleic acid.

38. The method of claim 7 wherein the dye labels include fluorescent dye labels.

39. The method of claim 21, wherein said one of the photoligating nucleic acid and the nucleic acid to be photoligated, which is immobilized on a substrate, is a nucleic acid-or a peptide nucleic acid.

40. The method of claim 35, wherein the photoligating nucleic acid comprises a nucleic acid that is a nucleic acid or a peptide nucleic acid.

* * * * *